United States Patent [19]
Scott et al.

[11] Patent Number: 5,932,715
[45] Date of Patent: Aug. 3, 1999

[54] NUCLEOTIDE SEQUENCES ENCODING A CS2 PILIN PROTEIN

[75] Inventors: June R. Scott, Atlanta; Barbara Froehlich, Decatur, both of Ga.; Judy Caron, Morris Plains, N.J.

[73] Assignee: Emory University, Atlanta, Ga.

[21] Appl. No.: 08/483,101

[22] Filed: Jun. 7, 1995

[51] Int. Cl.$^6$ .......................... C12N 15/31; C07H 21/04; A61K 48/00

[52] U.S. Cl. ................ 536/23.7; 536/23.1; 536/23.4; 514/44; 530/350; 530/403; 435/69.1; 435/252.3; 435/252.33; 435/320.1; 435/172.1; 435/172.3; 435/172.2; 935/9; 935/10; 935/11; 935/71; 935/72; 935/73

[58] Field of Search ..................... 514/44; 536/23.1, 536/23.7, 23.4; 530/403, 350; 435/252.3, 252.33, 69.1, 320.1, 172.1, 172.3, 172.2; 424/93.1, 93.2; 935/9, 10, 11, 71, 72, 73

[56] References Cited

PUBLICATIONS

Wolf et al. (1989) *Infect. Immun.* 57:164–173.
Sommerfelt et al. (1992) *Infect. Immun.* 69:3799–3806.
Hamers et al. (1989) *Microbial Pathogenesis* 6:297–309.
Perez–Casal et al. (1990) *Infect. Immun.* 58:3594–3600.
Froehlich et al. (1994) *Molec. Microbiol.* 12:387–401.
Jordi et al. (1991) *FEMS Microbiol. Lett.* 80:265–270.
Jordi et al. (1992) *DNA Sequence* 2:257–263.
Boylan et al. (1988) *J. Gen Microbiol.* 134:2189–2199.
Scott et al. (1992) *Molec. Microbiol.* 6:293–300.
Smyth, C.J. (1984) *FEMS Microbiol. Lett.* 21:51–57.
Timmerman and Tu (1985) *Nucl. Acids. Res.* 13:2127–2139.
Ohtsubo and Ohtsubo (1978) *Proc. Natl. Acad. Sci. USA* 75:615–619.
Evans et al. (1977) *Infect. Immun.* 18:330–337.
Caron et al. (1990) *Infect. Immun.* 58:874–878.
Rudin et al. (1994) *Infect. Immun.* 62:4339–4346.
Willshaw et al. (1990) *FEMS Microbiol. Lett.* 68:255–260.
Willshaw et al. (1990) *Microbial Pathogenesis* 9:1–11.
Evans and Evans (1978) *Infect. Immun.* 21:638–647.
Smyth (1982) *J. Gen. Microbiol.* 128:2081–2096.
Caron et al. (1989) *Proc. Natl. Acad. Sci. USA* 86:963–967.
Caron et al. (1990) *Infect. Immun.* 58:3442–3444.
Savelkoul et al. (1990) *Microbial Pathogenesis* 8:91–99.
Perez–Casal et al Infection and Immunity 1990 vol. 58, (11), 3594–3600.

*Primary Examiner*—Paula K. Hutzell
*Assistant Examiner*—Khalid Masood
*Attorney, Agent, or Firm*—Greenlee, Winner and Sullivan, PC

[57] ABSTRACT

Provided herein is a nucleotide sequence encoding a CS2 pilin protein of enterotoxigenic *Escherichia coli*. Also provided herein are the nucleotide sequences of coding sequences linked to the CS2 coding sequence, which other coding sequences must be expressed to allow the synthesis and assembly of the CS2 pili on the cell surface.

12 Claims, No Drawings

NUCLEOTIDE SEQUENCES ENCODING A CS2 PILIN PROTEIN

This invention was made, at least in part, with funding from the United States National Institutes of Health. Accordingly, the United States Government may have certain rights in this invention.

FIELD OF THE INVENTION

The field of this invention is the area of vaccines and genes encoding bacterial virulence determinants, particularly those genes encoding pilin proteins and genes essential for the assembly of pili of enterotoxigenic *Escherichia coli*, most particularly the genes encoding CS2 pili and the linked genes essential for the assembly of CS2 pili.

BACKGROUND OF THE INVENTION

Diarrheal diseases are an important cause of death in infants and young children in developing countries. Diarrheal diseases are also an important cause of serious illness in the elderly or immune compromised adults, as well as in travelers to countries where sanitation is inadequate and where these diseases are endemic.

Enterotoxigenic *Escherichia coli* strains (ETEC) are a major cause of diarrheal disease. Accordingly, there is a need for a vaccine for preventing the diseases associated with these bacteria. Ideally, a vaccine generates a protective immune response in which it interferes with a very early step in the infectious process, for example, by preventing the attachment of the pathogenic bacterial cells to host tissue. In the case of ETEC, this attachment step is believed to be mediated by pili, which are long, proteinaceous structures extending out from the surface of the bacterial cells. The CS2 pili are believed to mediate attachment to and/or promote colonization of the human upper intestine.

Different human ETEC strains produce a number of serologically different types of pili. The pili differ in antigenic specificity and subunit (pilin) molecular weight. Among human ETEC strains there are CFA/I (colonization factor antigen 1), CS1 (coli surface antigen 1) and CS2 (coli surface antigen 2) [Evans and Evans (1978) *Infect. Immun.* 21:638–647; Smyth (1982) *J. Gen. Microbiol.* 128:2081–2096]. The latter two were initially grouped together as CFA/II, a term that also includes the fibrillar CS3 surface structures [Levine et al. (1984) *Infect. Immun.* 44:409–420]. These three pili types seem to form a family based on several kinds of data. Although present in different ETEC strains, they are all positively regulated by rns or a closely related gene [Caron et al. (1989) *Proc. Natl. Acad. Sci. USA* 86:963–967; Caron et al. (1990) *Infect. Immun.* 58:3442–3444; Savelkoul et al. (1990) *Microb. Pathogen.* 8:91–99]. Second, the N-terminal amino acid sequences of the major pilin proteins are almost identical for these three pili types and for CS4 and PCF1066 [Wolf et al. (1989) *Infect. Immun.* 57:164–173; Sommerfelt et al. (1992) *Infect. Immun.* 69:3799–3806]. Third, for CFA/I and CS1, the DNA sequences of the four genes required for pili expression show significant homology [Hamers et al. (1989) *Microbial Pathogenesis* 6:297–309; Perez-Casal et al. (1990) *Infect. Immun.* 58:3594–3600; Froehlich et al. (1994) *Molec. Microbiol.* 12:387–401; Jordi et al. (1991) *FEMS Microbiol. Lett.* 80:265–270; Jordi et al. (1992) *DNA Sequence* 2:257–263]. Additionally, both CS1 and CFA/I are determined by plasmid-borne genes.

Only the genes encoding CS1 have been analyzed for function. The morphogenesis of CS1 pili appears to differ from that of other pili in Gram negative bacteria, for example, the pap pili of the *E. coli* strains associated with pyelonephritis or the common type 1 pili. Only four genes are needed to express CS1 pili in *E. coli* K12 [Froehlich et al. (1994) supra]. The major pilin subunit, encoded by cooA, lacks the features of disulfide bonds and penultimate tyrosine residues common to many other pilins. Additionally, the CS1 and CFA/I proteins show no homology with any other known or predicted proteins in the databank [Scott et al. (1992) *Molec. Microbiol.* 6:293–300; Froehlich et al. (1994) *Molec. Microbiol.* 12:387–401]. Thus, no typical chaperonins can be identified on the basis of sequence comparisons. Therefore, the pili on human ETEC strains are believed to belong to a unique family of pilins.

Mutations in any one of cooA, cooB, cooC and cooD result in an absence of pili. Only mutation in cooA prevents pilin synthesis (Scott et al. (1992) supra; Froehlich et al. (1994) supra]. There is no candidate for a pilus-associated adhesion other than the pilin protein itself.

There is a long felt need in the art for vaccines useful in protecting against diarrheal disease resulting from infection with ETEC, including CS2 ETEC. Because of the serological diversity in pili of ETEC, an ETEC vaccine advantageously includes antigenic determinants (epitopes) from more than one pilus type to be effective against more than one type of ETEC infection, or a single vaccine can include one or more conserved antigenic determinants.

SUMMARY OF THE INVENTION

An object of the present invention is to provide a nucleotide sequence encoding a CS2 pilin from enterotoxigenic *Escherichia coli*. As specifically exemplified, the encoded CS2 pilin has a preprotein amino acid sequence as given in SEQ ID NO:3 from amino acids −23 to +147. The preprotein coding sequence is given in SEQ ID NO:1 from nucleotide 1255 to nucleotide 1764 (excluding the translation stop codon). The encoded mature CS2 pilin protein has a deduced amino acid sequence as given in SEQ ID NO:3 from amino acid 1 through amino acid 147. The exemplified coding sequence of the mature CS2 pilin is given in SEQ ID NO:1 from 1324 to nucleotide 1764 (excluding the translation stop codon).

It is an additional object of the invention to provide non-naturally occurring nucleic acid molecules for the recombinant production of CS2 pili. A further object of the invention is a non-naturally recombinant DNA molecule which carries all four genes of the CS2 pilin gene cluster. As specifically exemplified herein, the gene cluster is within the DNA sequence as given in SEQ ID NO:1, and in the presence of the rns gene product, this gene cluster directs the synthesis of CS2 pili.

It is a further object of this invention to provide non-naturally occurring nucleic acid molecules, i.e., recombinant polynucleotides (e.g., a recombinant DNA molecule) comprising a nucleotide sequence encoding a CS2 pilin, preferably having a mature amino acid sequence as given in SEQ ID NO:3 from amino acid 1 through amino acid 147 or having a precursor amino acid sequence as given in SEQ ID NO:3, amino acids −23 through 147. As specifically exemplified herein, the nucleotide sequence encoding a mature CS2 pilin is given in SEQ ID NO:1 nucleotides 1324 through 1767, or a precursor coding sequence SEQ ID NO:1 from nucleotides 1255 through 1767. The skilled artisan will understand that the amino acid sequence of the exemplified CS2 pilin protein can be used to identify and isolate additional, nonexemplified nucleotide sequences which will encode a protein of the same amino acid sequence as given in SEQ ID NO:3, from amino acid 1 through amino acid 147, or an amino acid sequence of greater than 90% identity thereto and having equivalent biological activity. When it is desired that the sequence encoding a CS2 pilin or other CS2 protein be expressed, then the skilled artisan will operably link transcription and translational control regulatory sequences to the coding sequences, with the choice of the regulatory sequences being determined by the host in which the coding sequence is to be expressed. With respect to a recombinant DNA molecule carrying a CS2 pilin coding sequence, the skilled artisan will choose a vector (such as a plasmid or a viral vector) which can be introduced into and which can replicate in the host cell. The host cell can be a bacterium, preferably *Escherichia coli*, or, alternatively, a yeast or mammalian cell.

In another embodiment, recombinant polynucleotides which encode one or more of the proteins Cot A, Cot B, Cot C, and Cot D, required for production of CS2 pili including, e.g., protein fusions or deletions, as well as expression systems are provided. Expression systems are defined as polynucleotides which, when transformed into an appropriate host cell, can express CS2 pilin or CS2 pili-related proteins. The recombinant polynucleotides possess a nucleotide sequence which is substantially similar to a natural CS2 pilin-encoding polynucleotide or a fragment thereof. Where CS2 pili assembly is desired, all four cot genes provided herein are expressed. Expression may be under the control of the promoter normally associated with these genes (and in the presence of a functional rns gene) or the cot gene cluster can be expressed under the regulatory control of a heterologous promoter. The preferred enteric bacterial host strain for pili production is a strain of *E. coli* (which contains and expresses the rns regulatory gene when expression is under the control of the cot operon promoter).

Further provided by the present invention are oligonucleotides and polynucleotides which are capable of hybridizing specifically, using standard conditions well understood by the skilled artisan, to CS2 ETEC genomic DNA (or to the cognate mRNA). It is understood that these nucleic acid molecules do not include those sequences within SEQ ID NO:1 which are homologous to IS1 or IS3 or which are homologous to the genetically unlinked rns gene. These CS2-specific sequences can also be used in the preparation of primers for use in the polymerase chain reaction (PCR) for the amplification of CS2 nucleic acid. Either hybridization or PCR can be adapted for use in the detection of CS2 ETEC bacteria in biological, food or environmental samples or in the diagnosis of disease caused by CS2 ETEC bacteria.

The polynucleotides include RNA, cDNA, genomic DNA, synthetic forms, and mixed polymers, both sense and antisense strands, and may be chemically or biochemically modified or contain non-natural or derivatized nucleotide bases. DNA is preferred. Recombinant polynucleotides comprising sequences otherwise not naturally occurring are also provided by this invention, as are alterations of a wild type CS2 pilin or CS2 pili gene cluster sequence, including but not limited to deletion, insertion, substitution of one or more nucleotides or by fusion to other polynucleotide sequences, provided that such changes in the primary sequence of the CS2 pilin protein do not alter the epitope(s) capable of eliciting protective immunity.

The present invention also provides for fusion polypeptides comprising a CS2 pilin or a portion thereof. Homologous polypeptides may be fusions between two or more pilin protein sequences or between the sequences of a pilin and a related protein. Likewise, heterologous fusions may be constructed which would exhibit a combination of properties or activities of the proteins from which they are derived. Potential fusion partners include, but are not limited to, immunoglobulins, ubiquitin, bacterial β-galactosidase, trpE, protein A, β-lactamase, alpha amylase, alcohol dehydrogenase and yeast alpha mating factor [Godowski et al. (1988) *Science*, 241, 812–816]. Fusion proteins are typically made by recombinant methods but may be chemically synthesized as well understood in the art.

Compositions and immunogenic preparations including, but not limited to, vaccines comprising recombinant CS2 pilin or CS2 pili derived from enterotoxigenic *Escherichia coli* or from a recombinant *E. coli* and a suitable carrier are provided by the present invention. Such vaccines are useful, for example, in immunizing a human against diarrheal disease resulting from infection by CS2 enterotoxigenic *E. coli*. The preparations comprise an immunogenic amount of a CS2 pilin protein or an immunogenic fragment thereof. Such vaccines can advantageously further comprise pilin proteins or antigenic determinants therefrom of one or more other serological types, including but not limited to, CS1, CS3, CS4, PCF1066 and/or CFA/I. By "immunogenic amount" is meant an amount capable of eliciting the production of antibodies, preferably conferring protective immunity directed against infection by enterotoxigenic *E. coli* with the same pilus types present in the vaccine with which an individual has been immunized.

DETAILED DESCRIPTION OF THE INVENTION

Abbreviations used herein for amino acids are standard in the art. The abbreviations for amino acid residues as used herein are as follows: A, Ala, alanine; V, Val, valine; L, Leu, leucine; I, Ile, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine.

CS2 pilin is the term given to the *E. coli* pilin protein having an amino acid sequence substantially as disclosed in SEQ ID NO:3. It is understood that "CS2 pilin" provides a specific immune reaction with CS2-specific antisera. "Cot A" and "CS2 pilin" are used interchangeably herein. The complete amino acid sequence of the exemplified CS2 pilin protein, including the signal peptide with which it is synthesized, is given in SEQ ID NO:3, from amino acid 1 through amino acid 147 (mature protein) and the amino acid sequence of the associated signal sequence is given in SEQ ID NO:3 from −23 to −1. In nature, these proteins are produced by enterotoxigenic *E. coli* and can be purified from cells or from culture supernatant or as recombinant expression products using the disclosure provided herein.

Recombinant CS2 pilin can be obtained by culturing host cells transformed with the recombinant polynucleotides comprising nucleotide sequences encoding CS2 pilin as described herein under conditions suitable to attain expression of the pilin-encoding sequence.

The purification of CS2 pili has been described in Smyth, C. J. (1982) *J. Gen. Microbiol.* 128:2081–2086; Smyth, C. J. (1984) *FEMS Microbiol Lett.* 21:51–57. Although the published purification is for pili removed from the surface of CS2 cells, CS2 pilin can also be purified from the recombinant host cells (preferably bacterial cells, most preferably *E. coli*) which express the pilin gene but do not assemble pili on the cell surface using modifications of the aforementioned purification procedures and/or other modifications readily apparent to one of ordinary skill in the art.

The cloned DNA carrying the CS2 gene cluster was identified using a CS2-specific antibody screen of the cosmid library made with total *E. coli* C91f-6 DNA. The functional expression of the CS2 pili was confirmed by a positive hemagglutination assay. The CS2 gene cluster was shown to be contained on a DNA fragment of about 5.7 kb and produces functional CS2 pili as measured by hemagglutination.

The DNA sequence of the 5.7 kb fragment was determined (See SEQ ID NO: 1). The CS2 gene cluster has 39% G+C, which is significantly lower than the 50% value for the *E. coli* genome as a whole. Analysis of that sequence revealed four open reading frames (ORFs) which appeared to be expressed under the control of one promoter region. The four ORFs were named cotA, cotB, cotC and cotD, with "cot" being a mnemonic for coli surface antigen two.

The first ORF (cotB) is at nucleotides 499–1212 in SEQ ID NO:1; it is 714 bases in length and is preceded by a potential ribosome binding site (AAGG) beginning at about 16 bp upstream of the ATG translation start site. The deduced amino acid sequence for this ORF is given in SEQ ID NO:2 and contains 238 amino acids. The amino acid sequence appears to contain an 18 amino acid signal sequence. Processing at the predicted signal peptide cleavage site generates a predicted protein of 24.8 kDa in the periplasm of the bacterial cell. The mature protein is encoded at nucleotides 553–1212, and the signal peptide is encoded as nucleotides 499–552 of SEQ ID NO:1.

The second ORF (cotA) is 510 nucleotides in length (corresponding to nucleotides 1255–1764 of SEQ ID NO:1) and encodes a predicted protein of 147 amino acids, preceded by a signal peptide of an additional 23 amino acids. The deduced amino acid sequence is presented in SEQ ID NO:3. The first 30 amino acids of the predicted mature protein correspond exactly to the N-terminal amino acid sequence previously determined [Smyth et al. (1990) in *Microbial Surface Components and Toxins in Relation to Pathogenesis*, Ron and Rottern, Eds., Plenum Press, London]. The cotA open reading frame is preceded by a typical ribosome binding site sequence (TAAGG) which begins about 14 bp upstream of the ATG translation initiation codon. The mature protein is encoded at nucleotides 1324–1764, and the signal peptide is encoded at nucleotides 1255–1323 of SEQ ID NO:1.

The third coding sequence in the CS2 cluster, termed cotC herein, is 2598 nucleotides in length (nucleotides 1836–4433 of SEQ ID NO:1). There is a potential ribosome binding site sequence (AAG) starting at 14 bp upstream of the ATG translation start codon. This ORF is predicted to generate a mature protein of about 94.6 kDa after cleavage of a signal peptide of 26 amino acids (see SEQ ID NO:4). The mature protein is encoded at nucleotides 1914–4433, and the signal peptide is encoded at nucleotide 1836–1913 of SEQ ID NO:1.

The fourth ORF (cotD) is 1092 nucleotides in length (nucleotides 4451–5542 in SEQ ID NO:1). The potential translation initiation codon, associated with a candidate ribosome binding site sequence (GAGGT) about 10 bp upstream, is the less frequently used TTG codon. The deduced amino acid sequence (SEQ ID NO:5) generates a predicted mature protein of 364 amino acids (38.9 kDa) after cleavage of an 18 amino acid signal sequence. The mature protein is encoded at nucleotides 4505–5542, and the signal peptide is encoded at nucleotides 4451–4504 of SEQ ID NO:1.

A search of the combined Genbank databases using Blast software and the coding sequences from the CS2 gene cluster showed only significant homologies to the corresponding coding sequences of other human ETEC pili operons. There was significant homology of CotB to CooB (54% identical and 72% similar) and CfaA (52% identical and 71% similar), the first genes in the CS1 and CFa/I pili gene clusters, respectively [Jordi et al. (1991) *FEMS Microbiol. Lett.* 80:265–270; Hamers et al. (1989) *Microbial Pathogenesis* 6:297–309]. The hydropathy profiles for the three proteins were similar, but the calculated pI for CotB is much lower (8.58) than for CooB (10.32) or CfaA (10.22). Table 1 presents a comparison of the amino acid sequences of the CooB (from CS1 ETEC), CotB (from CS2 ETEC) and CfaA (from Cfa/I ETEC) proteins (SEQ ID NO:12, SEQ ID NO:2, and SEQ ID NO:13, respectively).

Mature CotA, the CS2 pilin protein, was found to have significant amino acid homology to mature CooA (50% identical and 64% similar) and mature CfaB (51% identical and 68% similar) ETEC pilins. Furthermore, the N-terminal amino acid sequence of mature CS2 (CotA) pilin has significant homology with CS4 and PCF1066 pilins. The predicted hydrophobicity plots of the CotA, CooA and CfaB pilins are very similar, and the predicted pI values are all within the range between 4.86 and 5.5. Although there is some homology, these proteins appear serologically distinct, although McConnell et al (1989) *FEMS Microbiol. Lett.* 61:105–108 reports some weak cross-reactivity. Table 2 presents a comparison of the amino acid sequences of the CooA (CS1 pilin), CotB (CS2 pilin) and CfaA (Cfa/I pilin) proteins (SEQ ID NO:10, SEQ ID NO:3, and SEQ ID NO:11, respectively).

The predicted mature CotC protein shows significant amino acid sequence homology to the corresponding gene products of the third open reading frames of the CS1 and CfA/I gene clusters (CooC and CfaC, respectively) [Froehlich et al. (1994) *Molec. Microbiol.* 12:387–401; Jordi et al. (1992) supra], but the signal sequences of the preproteins exhibit little amino acid sequence homology. Mature CotC exhibits 58% identity and 73% similarity to CooC and 56% identity and 72% similarity to CfaC. The predicted pI values are 6.53, 5.36 and 6.88 for CotC, Cooc and CfaC, respectively, and the hydrophobicity plots for the three proteins are very similar. Table 3 presents a comparison of the amino acid sequences of the CooC (from CS1 ETEC), CotC (from CS2 ETEC) and CfaC (from Cfa/I ETEC) proteins (SEQ ID NO:14, SEQ ID NO:4, and SEQ ID NO:15, respectively).

The third genes of the three clusters have several properties in common with those of other outer membrane proteins [for review, see Nikaido and Vaara (1985) *Microbiol. Rev.* 49:1–32; Jap and Walian (1990) *Quart. Rev. Biophys.* 23:367–403]. All three proteins have high predicted beta-sheet and low predicted alpha-helix contents as determined using the algorithm of Rost and Sander (1992) *Nature* 360:540; Rost and Sander (1993) *J. Molec. Biol.* 232:584–599; Sander and Schneider (1991) *Proteins: Structure, Function and Genetics* 9:56–68. These proteins have a relatively high content of charged amino acids and appear to lack extensive hydrophobic regions. Thus, it is concluded that CotC, CooC and CfaC are outer membrane proteins.

Limited homology was observed between CotC and other characterized outer membrane proteins including the Cfa1A protein of *Yersinia pestis*, which protein is involved in capsule biogenesis, a process deemed by some to be similar to pili formation [Karlyshev et al. (1994) *FEBS Lett.*

297:77–80]. There is also limited homology to FanD and FimD, large outer membrane proteins required for the assembly of the K99 pili of animal ETEC strains and the type 1 pili of *Salmonella typhimurium*, which proteins in turn have some homology with a protein required for dissociation of subunits from a chaperonin. CooC has been shown to be required for the assembly of CS1 pili [Froelich et al. (1994) supra]. Without wishing to be bound by any particular theory, it is postulated that CotC functions in the transport of growing pili through the outer membrane.

The only sequences similar to CotD in GenBank are the fourth genes of the CS1 and CFA/I gene clusters, CooD and CfaE [Froehlich et al. (1994) supra; Jordi et al. (1992) supra]. Mature CotD is 52% identical and 67% similar to mature CooD and 50% identical and 68% similar to mature CfaE. The predicted hydrophobicities are very similar, but the predicted pI values of the mature proteins differ: 7.07 for CotD, 6.97 for CooD, and 9.22 for CfaE. Table 4 presents a comparison of the amino acid sequences of the CooD (from CS1 ETEC), CotD and CfaE (from Cfa/I ETEC) proteins (SEQ ID NO:16, SEQ ID NO:5, and SEQ ID NO:17, respectively).

The region upstream of the CS2 gene cluster coding sequences contains the promoter for at least the first gene (cotB) of the CS2 gene cluster and possibly includes regulatory elements. Part of the upstream region (nucleotides 1–369 of SEQ ID NO:1 is 99% homologous with the last 369 bases of the IS3 insertion sequence [Timmerman and Tu (1985) *Nucl. Acids Res.* 13:2127–2139]. Directly following the IS3 homology is a region (nucleotides 369–401 of SEQ ID NO:1) which is 100% homologous with bases 73–41 of IS1 [Ohtsubo and Ohtsubo (1978), *Proc. Natl. Acad. Sci. USA* 75:615–619]. There is a potential promoter (bases 422–451 of SEQ ID NO:1) upstream of the CotB open reading frame (which begins at nucleotide 499). This promoter is very likely to be utilized since both the −35 (gTGACA) and the −10 (TATcAT) regions match the consensus in 5 of 6 bases, and the spacing of 18 bases between the two regions is acceptable [Pribnow (1979) in *Biological Regulation and Development*, Vol. I, R. F. Goldberger, Ed., Plenum Press, NY and London, pp. 219–277; Hawley and McClure (1983) *Nucl. Acids Res.* 11: 2237–2255].

SEQ ID NO:1 extends 253 nucleotides beyond the stop codon of cotD. There are no open reading frames within this region, and a search of Genbank revealed no significant homology to any sequence therein.

Surprisingly, in an *E. coli* K12 genetic background, cotA cotB cloned under the regulatory control of the lac promoter appeared to produce relatively small amounts of CotA (CS2 pilin). Similarly, cotA alone also yielded small amounts of CS2 pilin protein even when expressed under the regulatory control of a heterologous promoter.

Oligonucleotides and polynucleotides which are capable of hybridizing specifically, using standard conditions well understood by the skilled artisan, to CS2 ETEC genomic DNA (or to the cognate mRNA) can be readily prepared using the CS2 sequence information provided herein (See SEQ ID NO:1 and the remainder of the present disclosure). It is understood that these nucleic acid molecules do not include those sequences within SEQ ID NO:1 which are homologous to IS3 or which are homologous to the genetically unlinked rns gene. These CS2-specific sequences can also be used in the preparation of primers for use in the polymerase chain reaction (PCR) for the amplification of CS2 nucleic acid. Either hybridization or PCR can be adapted for use in the detection of CS2 ETEC bacteria in biological, food or environmental samples or in the diagnosis of disease caused by CS2 ETEC bacteria. Where conditions for hybridization of the oligonucleotide or polynucleotide probe or primer, it is possible to obtain binding of the probe or primer to CS1 or Cfa/I pilin operon DNA. The skilled artisan can, using DNA sequence information provided herein and available in the prior art and with the choice of the proper positive and negative experimental controls, select the appropriate portion(s) of SEQ ID NO:1 to achieve the desired result of detection of or amplification of the selected target CS2, CS1, or Cfa/I nucleic acid. The appropriate adaptation of the technology allows the diagnosis of human ETEC disease caused by CS2, CS1 or Cfa/I bacteria (for example, using stool samples from a person having the symptoms of ETEC disease) as well as the detection of those bacteria in food, environmental or biological samples.

Because the gene products needed for CS2 and CS1 pili production share some homology, we determined whether they can complement each other for production of functional pili. Compatible plasmids were constructed to contain the A and B genes from one cluster and the C and D genes from the other. In these plasmids, the coo and cot genes were expressed from the lac promoter (see Example 2).

All complementation experiments were done in mutant derivatives of the ETEC-derived strain LMC10, which contains the genes for CS1 pili. Two mutants of LMC10 were used. The first, JEF100, expresses no coo gene products because it contains an omega insertion in the first gene in the cluster (cooB), which insertion is polar on the expression of downstream genes [Scott et al. (1992) *Mol. Microbiol.* 6: 293–300]. JEF100 does not express pili, but the coo genes act in trans to complement this mutant for production of CS1 pili. For this complementation test, the cotA and B products were produced from pEU555, and the cooC and D products were produced from pEU478 in the JEF100 genetic background. Although JEF100 carrying either plasmid alone produces no visible pili, JEF100/pEU555/pEU478 was highly piliated, indicating the cotA and B gene products can interact with cooC and D gene products to assemble pili.

In the reciprocal experiment, a different LMC10 mutant was used. Strain FAK001 contains an omega insertion in cooC, so it expresses no CooC and little or no CooD. In the presence of a plasmid producing Rns, the positive regulator of the CS1 and CS2 genes, FAK001 expresses CooB and CooA [Froehlich et al. (1994) supra]. FAK001/pEU2040 (a plasmid producing Rns) makes no visible pili. In the homologous complementation, pili are produced. Strain FAK001 carrying pEU2030 (which expresses Rns) and pEU478, which expresses CooC and D, is highly piliated. In the heterologous complementation, when pEU582, which encodes cotC and D, is present in FAK001/pEU2040, many pili are also produced. Thus the cooA and cooB gene products can also interact with the cotC and D gene products to form apparently normal pili.

Because cooC and cooD can substitute for cotC and cotD, and vice versa, strains which express both CS1 and CS1 can be constructed by introducing cotA and cotB into a genetic background which is Rns+, CooC+ and CooD+, and more preferably is deregulated for CS1 and/or CS2 pilin production. Similarly, the cooA and cooB genes can be introduced into a strain which is CotC+ CotD+ and is preferably deregulated for pilin production.

SEQ ID NO:1, nucleotides 1255–1764, presents an exemplified coding sequence for CS2 pilin with its associated 23 amino acid signal peptide. However, it is understood that there will be some variations in the amino acid sequences and encoding nucleic acid sequences for CS2 pilin from other CS2 ETEC strains. The ordinary skilled artisan can readily identify and isolate nonexemplified CS2 pilin-encoding sequences from other ETEC strains where there is at least 90% homology to the CS2 pilin coding sequence disclosed herein using this sequence taken with what is well known to the art. Those other sequences encode a pilin protein cross-reacting with and sharing antigenic determinants identical to those of the CS2 pilin exemplified herein.

It is understood by the skilled artisan that there can be limited numbers of amino acid substitutions in a protein without significantly affecting either function or antigenic cross reaction and specificity, and that nonexemplified CS2 pilin proteins can have some amino acid sequence divergence from the exemplified amino acid sequence (SEQ ID NO:13, amino acids 1–147). Such naturally occurring variants can be identified, e.g., by hybridization to the exemplified (mature) CS2 coding sequence (or a portion thereof capable of specific hybridization to CS2 pilin sequences) under conditions appropriate to detect at least about 90% nucleotide sequence homology, preferably about 95% homology. A requirement readily apparent to the skilled artisan is that a nonexemplified CS2 protein must be capable of generating protective immunity against ETEC of the CS2 serological type.

It is well known in the biological arts that certain amino acid substitutions can be made in protein sequences without affecting the function of the protein. Generally, conservative amino acids are tolerated without affecting protein function. Similar amino acids can be those that are similar in size and/or charge properties, for example, aspartate and glutamate, and isoleucine and valine are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of different evolutionary sources.

The skilled artisan recognizes that other ETEC strains can have coding sequences for a pilin protein with the distinguishing characteristics of a CS2 pilin; those coding sequences may be identical to or synonymous with the exemplified coding sequence, or there may be some variation(s) in the encoded amino acid sequence. The distinguishing characteristics of CS2 pili or pilin are specific binding to CS2-specific antiserum and the ability to mediate mannose-resistant hemagglutination of bovine erythrocytes. It is noted that not all bovine erythrocytes are agglutinated by CS2 pili. Accordingly, it is understood by the skilled artisan that samples of bovine blood must be pre-tested with CS2-positive and CS2-negative controls prior to selection and use in such experiments. A CS2 pilin coding sequence from an ETEC strain other than C91f can be identified by, e.g., hybridization to a polynucleotide or an oligonucleotide having the whole or a portion of the exemplified coding sequence, under stringency conditions appropriate to detect a sequence of at least 90% homology, and where the expression product of said other coding sequence reacts specifically with the CS2-specific antiserum. In view of the similarity of the N-terminal amino acid sequences of ETEC pilin proteins (i.e., for CS1, CS2, CS4, PCF1066 and CFA/I pilins) the skilled artisan understands that a CS2-specific probe is directed to a portion of the coding sequence other than the 5' end of the pilin coding sequence. Similarly, it is understood that the portions of the CS2 gene cluster nucleotide sequence which have strong homology to a noncoding region of the unlinked rns locus or to IS3 or IS1 are also not appropriate to use as a hybridization probe for CS2 pilin coding sequences.

A polynucleotide or fragment thereof is "substantially homologous" (or "substantially similar") to another polynucleotide if, when optimally aligned (with appropriate nucleotide insertions or deletions) with another polynucleotide, there is nucleotide sequence identity for approximately 80% of the nucleotide bases, usually approximately 90%, more preferably about 95% to 100% of the nucleotide bases.

Alternatively, substantial homology (or similarity) exists when a polynucleotide or fragment thereof will hybridize to another polynucleotide under selective hybridization conditions. Selectivity of hybridization exists under well known experimental conditions which allow one to distinguish the target polynucleotide of interest from other polynucleotides. Typically, selective hybridization can be effected when there is approximately 75% similarity over a stretch of about 14 nucleotides, preferably approximately 65%, more preferably approximately 75%, and most preferably approximately 90%. See Kanehisa (1984) *Nucl. Acids Res.* 12:203–213. The length of homology comparison, as described, may be over longer stretches, and in certain embodiments will often be over a stretch of about 17 to 20 nucleotides, and preferably about 36 or more nucleotides.

The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1M, typically less than 500 mM, and preferably less than 200 mM. However, the combination of parameters is much more important than the measure of any single parameter (Wetmur and Davidson (1968) *J. Mol. Biol.* 31, 349–370).

An "isolated" or "substantially pure" polynucleotide is a polynucleotide which is substantially separated from other polynucleotide sequences which naturally accompany a native CS2 sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to "encode" a polypeptide if, in its native state or when manipulated by methods known to those skilled in the art, it can be transcribed and/or translated to produce the polypeptide of a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as transcription activators, may be operably linked even at a distance, i.e., even if not contiguous.

The term "recombinant" polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate nonexemplified CS2 pilin coding sequences. Probes comprising synthetic oligonucleotides or other polynucleotides may be derived from naturally occurring or recombinant single- or double-stranded nucleic acids or be chemically synthesized. Polynucleotide probes may be labelled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a CS2 pilin or a fragment thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli*, although other prokaryotes, such as Salmonella, Shigella, Vibrio or *Bacillus subtilis* may also be used. Mammalian or other eukaryotic host cells include yeast, filamentous fungi, plant, insect, amphibian and avian species. Such factors as ease of manipulation, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.* 22: 1859–1862 or the triester method according to Matteuci et al. (1981) *J. Am. Chem. Soc.* 103: 3185, and may be performed on commercial automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e., vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides from the CS2 pilin coding sequence or from secreted polypeptides of the same or related species, are included, where appropriate, to allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1987) *Current Protocols in Molecular Biology*, Greene Publishing and Wiley Interscience, New York; and Metzger et al. (1988) *Nature* 334: 31–36. Many useful vectors for expression in bacteria, yeast, mammalian, insect, plant or other cells are well known in the art and may be obtained from such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The recombinant vectors containing the CS2 coding sequence of interest can be introduced into the host cell by any of a number of appropriate means, including conjugation, electroporation, transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with CS2 pilin-encoding polynucleotides of the present invention in compatible vectors or other expression vehicles and culturing such transformed host cells under conditions suitable to attain expression of the CS2 pilin-encoding sequence. The CS2 pilin may then be recovered from the host cell and purified.

The coding sequence for the mature CS2 pilin (CotA) is expressed after PCR site-directed mutagenesis and cloning into an expression vector suitable for use in *E. coli* in which the genes encoding Rns and preferably CotB, CotC or CooC and CotD or CooD are also expressed. Advantageously, the coding sequence also includes the information for a signal peptide. The signal peptide is removed during synthesis and localization by the cellular membrane proteins of the recombinant host cell. Exemplary expression vectors for *E. coli* and other host cells are given, for example, in Sambrook et al. (1989), vide infra, and in Pouwels et al. (Eds.) (1986) *Cloning Vectors*, Elsevier Science Publishers, Amsterdam, the Netherlands.

When it is desired to eliminate leader sequences and precursor sequences at the 5' side of the coding sequence, a combination of restriction endonuclease cutting and site-directed mutagenesis via PCR using an oligonucleotide containing a desired restriction site for cloning (one not present in coding sequence), a ribosome binding site, an translation initiation codon (ATG) and the codons for the first amino acids of the mature CS2 pilin. The oligonucleotide for site-directed mutagenesis at the 3' end of the coding sequence for CS2 pilin includes nucleotides encoding the carboxy-terminal amino acids of CS2 pilin, a translation termination codon (TAA, TGA or TAG), and a second suitable restriction endonuclease recognition site not present in the remainder of the DNA sequence to be inserted into the expression vector. The site-directed mutagenesis strategy is similar to that of Boone et al. (1990) *Proc. Natl. Acad. Sci. USA* 87: 2800–2804, as modified for use with PCR.

In another embodiment, polyclonal and/or monoclonal antibodies capable of specifically binding to CS2 pilin or fragments thereof are provided. The term antibody is used to refer both to a homogenous molecular entity, or a mixture such as a serum product made up of a plurality of different molecular entities. Monoclonal or polyclonal antibodies specifically reacting with the CS2 pilin may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987) supra. Also, recombinant immunoglobulins may be produced by methods known in the art, including but not limited to the methods described in U.S. Pat. No. 4,816,567, incorporated by reference herein. Monoclonal antibodies with affinities of $10^8$ M$^{-1}$, preferably $10^9$ to $10^{10}$ or more are preferred.

Antibodies generated against CS2 peptide antigen and specific for CS2 pilin are useful, for example, as probes for screening DNA expression libraries or for detecting the presence of ETEC expressing CS2 pili in a test sample. Hydrophilic regions of the CS2 pilin can be identified by the skilled artisan [See, e.g., *Antibodies: A Laboratory Manual*, Harlow and Lane, eds., Cold Spring Harbor Laboratory, Cold Spring Harbor, N.Y.], and peptide antigens can be synthesized and conjugated to a suitable carrier protein (e.g., bovine serum albumin or keyhole limpet hemocyanin) for use in vaccines or in raising antibody(ies) specific for CS2-expressing ETEC. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include but are not limited to U.S. Pat. Nos. 3,817,837; 3,850,752; 3,939,350; 3,996,345; 4,277,437; 4,275,149; and 4,366,241.

Antibodies specific for CS2 pilin and/or pili, which are capable of inhibiting adherence of CS2-expressing ETEC cells to host tissue, are useful in preventing diarrheal disease resulting from CS2 ETEC infection. Such antibodies can be obtained by the methods described above.

Compositions and immunogenic preparations including vaccine compositions comprising substantially purified recombinant CS2 pili or CS2 pilin protein and a suitable carrier therefor are provided. Alternatively, hydrophilic regions of the CS2 pilin can be identified by the skilled artisan, and peptide antigens can be synthesized and conjugated to a suitable carrier protein (e.g., bovine serum albumin or keyhole limpet hemocyanin) for use in vaccines or in raising antibody(ies) specific for CS2-expressing ETEC.

Alternatively, a suitable recombinant vector or recombinant host bacterium (such as a suitable Vaccinia virus or Mycobacterium) which carries an expressible gene encoding CS2 pilin or the CS2 pilin operon can be incorporated into a composition for immunizing a human. The coding sequence for at least one of CotA, CotB, CotC and CotD, preferably CotA (CS2 pilin) and optionally all four, can be incorporated into a recombinant nucleic acid molecule for use in a DNA vaccine preparation, termed a vaccine DNA preparation herein. Such a recombinant nucleic acid molecule (e.g., DNA) contains an origin of replication functional in human cells (e.g., an SV40 origin) and the coding sequence(s) is (are) operably linked to transcription regulatory elements such that when the recombinant DNA molecule is introduced into human cells, expression of the coding sequence(s) results. Optionally, there can be an origin of replication functional in a bacterium such as *E. coli* to facilitate cloning and amplification. When the vaccine DNA preparation is introduced into human cells in vivo, the coding sequence(s) is (are) expressed with the result that an immune response is raised to the protein expression product, and the vaccinated human develops immunity against CS2 ETEC infection and disease. The vaccine DNA preparation is formulated as known to the art, and the vaccine recombinant DNA molecules can be introduced into human cells in vivo or ex vivo. Ballistic transformation, liposome-mediated transformation, transfection, injection or any other means known to the art can be used to introduce the vaccine DNA molecules into human cells.

Immunogenic compositions are those which result in specific antibody production when injected into a human or an animal. Such immunogenic compositions are useful, for example, in immunizing a human against infection by CS2 ETEC. The immunogenic preparations comprise, or result in the expression of an immunogenic amount of one or more ETEC pilin or an immunogenic fragment(s) or subunit(s) thereof. Such immunogenic compositions may comprise one or more ETEC pilins, or in combination with another protein or other immunogen. By "immunogenic amount" is meant an amount capable of eliciting the production of antibodies directed against ETEC pilin, including but not limited to CS2 pilin in an individual to which the vaccine has been administered. Vaccines or immunogenic compositions comprising CS2 pili or pilin may also advantageously comprise other ETEC antigenic determinants, for example, pili or pilins of CS1, CS3, CS4, and Cfa and/or other serological types.

Immunogenic carriers may be used to enhance the immunogenicity of the CS2 pili or pilin. Such carriers include but are not limited to proteins and polysaccharides, liposomes, and bacterial cells and membranes. Protein carriers may be joined to the pilin sequences to form fusion proteins by recombinant or synthetic means or by chemical coupling. Useful carriers and means of coupling such carriers to polypeptide antigens are known in the art. The art knows how to administer immunogenic compositions so as to generate protective immunity on the mucosal surfaces of the gastrointestinal tract, where immunity specific for ETEC, and particularly CS2 type ETEC, is most helpful.

The immunogenic compositions may be formulated by any of the means known in the art. Such vaccines are typically prepared as injectables, either as liquid solutions or suspensions. Solid forms suitable for solution or suspension in liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration are known in the art and can also be used.

CS2 pilin or pili and/or fragments thereof may be formulated into immunogenic compositions as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylaminoethanol, histidine, and procaine.

The immunogenic CS2 pilin or pili (or peptide antigens thereof) compositions are administered in a manner compatible with the dosage formulation, and in such amount as will be prophylactically and/or therapeutically effective. The quantity to be administered, which is generally in the range of about 100 to 1,000 µg of protein per dose, more generally in the range of about 5 to 500 µg of protein per dose, depends on the subject to be treated, the capacity of the individual's immune system to synthesize antibodies, and the degree of protection desired. Precise amounts of the active ingredient required to be administered may depend on the judgment of the physician and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

All references cited herein are hereby incorporated by reference in their entirety.

Except as noted hereafter, standard techniques for cloning, DNA isolation, amplification and purification, for enzymatic reactions involving DNA ligase, DNA polymerase, restriction endonucleases and the like, and various separation techniques are those well known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

The foregoing discussion and the following examples illustrate but are not intended to limit the invention. The skilled artisan will understand that alternative methods may be used to implement the invention.

EXAMPLES

Example 1
Bacterial Strains and Plasmids

ETEC strain C91f-6 is a spontaneous CS2 pilus-deficient derivative of the wild-type ETEC strain C91f, which expresses CS2 [Smyth (1982) *J. Gen. Microbiol.* 128:2081–2096; Smyth (1984) *FEMS Microbiol. Lett.* 21:51–57]. Strain LMC10 is a lac deletion, restriction-deficient derivative of the ETEC-derived C921b-2 strain [Caron et al. (1989) supra]. Strain JEF100 is a derivative of LMC10 which contains the cooB1 allele in place of the wild type cooB [Scott et al. (1992) *Mol. Microbiol.* 6:293–300]. The cooB1 allele contains an insertion of a kanamycin resistance omega fragment; the insertion mutation has polar effects, i.e., it inhibits the transcription and translation of downstream cistrons. Strain FAK001 is a LMC10 derivative in which there is a tetracycline resistance omega fragment inserted into cooC [Froelich et al. (1994) *Mol. Microbiol.* 12:387–401].

E. coli K-12 strains MC4100 and DH5alpha [Casadaban, M. (1976) *J. Mol. Biol.* 104:557–566; Sambrook et al. (1989) supra] are used as host strains for cloning.

For most experiments bacteria are grown in Luria-Bertani (LB) broth as described [Scott (1974) *Virology* 62:344–349]. For hemagglutination assays and for electron microscopy, bacteria are grown on CFA agar [Evans et al. (1977) *Infect. Immun.* 18:330–337. Antibiotic supplementation, where necessary, is with ampicillin (50 µg/ml), chloramphenicol (40 µg/ml), kanamycin (40 µg/ml) or tetracycline (10 µg/ml).

The cosmid vector pHC79, which confers resistance to ampicillin [Collins and Hohn (1980) *Gene* 11:291–298], is used for the cloning of the genomic sequences containing the CS2 gene cluster. The high copy number vector pUC19, which also carries a gene conferring resistance to ampicillin [Messing and Vieira (1982) *Gene* 10:269–276], and the low copy number pSC101-based vector pHSG576, which confers resistance to chloramphenicol [Takeshita et al. (1987) *Gene* 61:63–74], are used for subcloning. The rns-containing plasmids used in these experiments are pEU2030 (rns cloned into pUC18) [Caron et al. (1989) *Proc. Natl. Acad. Sci. USA* 86:963–967], pEU2040 with rns cloned into pHSG576 [Perez-Casal et al. (1990) *Infect. Immun.* 58:3594–3600] and pEU2021 with rns cloned into pBR322 [Caron et al. (1989) supra]. Plasmid pEU478 contains cooC and cooD cloned under the regulatory control of the lac promoter in pHSG576 [Froelich et al. (1994) supra].

For CS2 expression, *E. coli* cells are grown at temperatures over 25° C., typically at 37° C.

Example 2
Immunological Techniques and Reagents and Hemagglutination Assays

Anti-CS2 polyclonal antibodies are prepared in rabbits as described by Scott et al. (1992) *Molec. Microbiol.* 6:293–300. C91f-6(pEU2021) cells are used as antigen for immunizing the rabbits. Antibodies which are not specific for the CS2 pili are removed by adsorption with sonicated cells of *E. coli* strains MC4100 and LMC10.

Sodium dodecyl sulfate-polyacrylamide gel electrophoresis (SDS-PAGE) of 12.5% gels is performed as in Laemmli (1970) *Nature* 227: 680–685. After SDS-PAGE, protein bands are transferred to nitrocellulose membranes, and immunoblotting is done using CS2-specific antiserum according to the protocol of Perez-Casal et al. (1989) *Infect. Immun.* 58:3594–3600. Total protein patterns are visualized with Coomassie blue staining or by the silver staining method [See, e.g., Merril et al. (1979) *Proc. Natl. Acad. Sci USA* 76, 4335–4340].

Hemagglutination assays using selected bovine erythrocytes are carried out in the presence of 100 mM mannose as described by Caron et al. (1989) *Proc. Natl. Acad. Sci. USA* 86:963–967. Not all bovine erythrocytes are agglutinated by CS2 pili. Accordingly, samples of bovine blood must pe pre-tested with CS2-positive and CS2-negative controls prior to selection and use in CS2 hemagglutination experiments. Equal volumes of 3% suspension of washed bovine erythrocytes and pelleted bacterial cells (grown overnight at 37° C. in LB are mixed and observed for hemagglutination after 30 minutes. A positive hemagglutination reaction is indicative of the expression of CS2 pili.

Example 3
Construction and Screening of the Total DNA library

A library is constructed using *E. coli* C91f-6 total DNA partially digested with Sau3A to give fragments of about 30–45 kb in size and BamHI-cut pHC79 cosmid DNA. After ligation the recombinant DNA molecules are packaged into lambda particles using a lambda packaging extract system (Gigapack, Stratagene, La Jolla, Calif.). Then the packaged recombinant cosmid particles are used to transduce *E. coli* DH5α containing pEU2040. Three of 452 ampicillin-resistant, chloramphenicol-resistant colonies react positively when tested by colony immunoblot analysis with CS2-specific antiserum. One isolate which is confirmed by Western blotting to contain CS2 antigen in heat extracts is studied further. This isolate contains a CS2-positive plasmid called pEU5006. After digestion of pEU5006 with PstI and EcoRV, a 5.7 kb fragment is isolated. This fragment is then ligated into pUC19 (which had been cut with PstI and SmaI) to yield pEU588. Said 5.7 kbp fragment has the nucleotide sequence of SEQ ID NO:1.

The following plasmids effect the expression of the CS2 genes under the regulatory control of the lac promoter of the vector. A 6.0 kbp ClaI/EcoRI fragment of PEU588 is made bluntended and ligated to SmaI-cut pUC19; this fragment contains the cotA and cotB genes. The EcoRI site of the fragment is about nucleotide 2753 of SEQ ID NO:1. pEU582 (containing cotC and cotD) is constructed by inserting a 4.0 PvuII fragment (extending from nucleotide 1642 to nucleotide 5591 of SEQ ID NO:1) into SmaI-cut pUC19. The presence and orientations of all inserts are confirmed by restriction endonuclease analysis.

Standard protocols for DNA library screening, plasmid phage purification, agarose gel electrophoresis and plasmid cloning were employed [Maniatis et al. (1982), supra].

Example 4
DNA Sequencing and Sequence Analysis

Double-stranded DNA is subcloned and sequenced by the dideoxy chain termination method [Sanger et al. (1977) *Proc. Natl. Acad. Sci. USA* 74, 5463–5467]. Oligonucleotide primers for sequencing reactions are synthesized by the phosphoramidite method with an Applied Biosystems model 394 automated DNA Synthesizer (Applied Biosystems, Foster City, Calif.).

Example 5
Electron Microscopy

Where it is desired to examine bacterial cells for the presence of pili, bacterial cells are grown at 37° C. on CFA agar supplemented with antibiotics to select for plasmid maintenance as necessary. A small sample of cells is suspended in 25 μl of a solution containing 1 Mm Tris-HCl (pH 7.5), 10 mM $MgCl_2$. The droplet of suspension is held for 60 minutes at room temperature. 10 μl of the sample is then diluted into 15 μl of the same Tris $MgCl_2$ solution, and formvar-coated carbon grids (200 mesh) are floated on the surface of the diluted cell mixture for 30 minutes. Excess liquid is absorbed from each grid using a paper wick, and each grid is then stained with ammonium phosphotungstate (pH 7.0). The grids are examined with a transmission electron microscope (Phillips Model 201) at 12000× magnification.

Table 1

Comparison of CooB, CotA and Cf&A Protein Sequences[1]

| | | | | | | |
|---|---|---|---|---|---|---|
| CotB | M.KiLlFviL | FfnvFaAsAN | FMVYPISKDI | qsGgSEtIkV | FSKSKDVQYI | (49) |
| CooB | MrKLF..LSL | LMiPFVAkAN | FMIYPISKEI | KgGsSELIRI | YSKSKDtQYI | (48) |
| CfaA | MhKLFyLLSL | LMaPFVAnAN | FMIYPISKDl | KnGnSELVRV | YSKSKEIQYI | (50) |
| Consensus | M-KLF---LSL | LM-PFVA-AN | FMIYPISKDI | K-G-SELIRV | YSKSKD-QYI | |
| CotB | KIYTKrVINP | GTKEEqEVDI | kNWDGGLIVT | PaKVVLPAGA | SKSIRLTein | (99) |
| CooB | KVYTKKVlNP | GTKEEYEVDt | PNWEGGLVtT | PsKVILPgGg | SKSVRLsQLK | (98) |

Table 1-continued

Comparison of CooB, CotA and CfaA Protein Sequences[1]

```
CfaA       KIYTKKIINP GTtEEYkVDI PNWDGGLVVT PqKVILPAGA SKSIRLTQFK    (100)

Consensus  KIYTKKVINP GTKEEYEVDI PNWDGGLVVT P-KVILPAGA SKSIRLTQ-K

CotB       kkeqEEVYRV YFESVKPggQ DdIeeKNgrv nTDLSVNIIY AALIRtsPen    (149)

CooB       dissEDVYRV YFESIKPEkQ Dgl.sKNKsL kTDLSVNIIY AALIRvLPkD    (147)

CfaA       ipkkEEVYRV YFEaVKPDsk EnV.idNKKL tTELSVNIIY AALIRsLPsE    (149)

Consensus  ----EEVYRV YFESVKP--Q D----KNK-L -TDLSVNIIY AALIR-LP--

CotB       pqrkLdVSie sn.NVwIKNT GNIRlGIKDV FLCdtTSI.N DkCAKfsYNr    (197)

CooB       gksdMraSls pKssllIKNT GNVRvGIKDa FFCKkTSINn DdCIKKtYNK    (197)

CfaA       qnisLnISrn aKkNIiIyNn GNVRaGVKDI YFCKssnI.d DnCVKKaYNK    (198)

Consensus  ----L--S-- -K-N--IKNT GNVR-GIKD- FFCK-TSI-N D-C-KK-YNK

CotB       NlYPDmSvDT kLgkkGFSYa vIDtkDDrnE nsGeLInIKl P              (238)

CooB       NIYPgsSFDT gvIqNGFShI FIDsvDgsaq KqGkrmlIsI h              (238)

CfaA       NIYPEkSFDT .LVnNnFSYV FIklnhEgiE KeqgLIqlKV P              (238)

Consensus  NITP--SFDT -L--NGFSY- FID--D---E K-G-LI-IK- P
```

[1]Amino acid sequence comparison was done using the PILEUP algorithm in the GCG Software. The conserved amino acids are in upper case letters; nonconserved amino acids are in lower case letters. Amino acids which are conserved in all three proteins are given in bold-face letters in the consensus amino acid sequence.

TABLE 2

Comparison of CooA, CotA and CfaB Protein Sequences[2]

```
CotA       MKLnKiIGAL vLsstFVsMG ASAaEKNITV TASVDPTIDL MQSDGtALPS    (50)

CooA       MKLKKTIGAM ALaTLFatMG ASAVEKtIsV TASVDPTVDL LQSDGsALPn    (50)

CfaB       MKFKKTIGAM ALtTMFVavs ASAVEKNITV TASVDPaIDL LQaDGnALPS    (50)

Consensus  MKLKKTIGAM AL-T-FV-MG ASAVEKNITV TASVDPTIDL LQSDG-ALPS

CotA       AVniAYlPge KrFESaRINT QVHTNnkTKG IqIKLtnDnv VMTNlsdPsk    (100)

CooA       sVaLtYSPAv nnFEahtINT vVHTNDsdKG VVVKLs.adP VLsNVLNPTl    (99)

CfaB       AVkLAYSPAs KtFESyRVmT QVHTNDaTKk VIVKLa.Dtp qLTdVLNsTv    (99)

Consensus  AV-LAYSPA- K-FES-RINT QVHTND-TKG V-VKL--D-P VLTNVLNPT-

CotA       tIPleVSFAG tkLSTaAtsI tAdqLNFgAa GVetVSaTkE LVInAgsTq.    (149)

CooA       QIPVSVnFAG kpLSTTgitI DsndLNFassS GVNkVSSTQk LsIhAdATrv    (149)

CfaB       QmPISVSWgG qvLSTTAkef EAaaLgYsAS GVNgVSSsQE LVIsA.Apkt    (148)

Consensus  QIP-SVSFAG --LSTTA--I -A--LNF-AS GVN-VSSTQE LVI-A-AT--

CotA       .qTnivAGNY QGLVSIVLTq ep                                  (170)

CooA       tGgAlTAGqY QGLVSIILTk st                                  (171)

CfaB       aGTApTAGNY sGvVSlVMTl gs                                  (170)

Consensus  -GTA-TAGNY QGLVSIVLT- --
```

TABLE 2-continued

Comparison of CooA, CotA and CfaB Protein Sequences[2]

[2]Amino acid sequence comparison was done using the PILEUP algorithm in the GCG Software. The conserved amino acids are in upper case letters; nonconserved amino acids are in lower case letters. Amino acids which are conserved in all three proteins are given in bold-face letters in the consensus amino acid sequence.

TABLE 3

Comparison of CooC, CotC and CfaC Protein Sequences[3]

```
CotC       M. .rafNKIt VfIlfiPGlC fGtnGleskk nIPEeFiDLW mEQDELLEVn  (48)
CooC       MiggKssKVV IvlSVliGsS sGfaBkynlv DIPESFRDLW GEQDELLEVr  (50)
CfaC       MkhkKkNrlV VaISValipY iGvtG..... DIPDSFRDLW GEQDEFyEVk  (45)
Consensus  M---K-NK-V V-ISV--G-- -G--G----- DIPESFRDLW GEQDELLEV- CotC       LYGrSLGVHR VlTTPTTVKF sSvEeILEKI NVKqEKkeDL RsLLlqSYSR  (98)
CooC       LYGQSLGVHR IKsTPTTVaF eSPDnlLDKI eInKgKEaDL RVLMrgSFqR  (100)
CfaC       LYGQtLGIHR IKTTPThIKF ySPEsILDKI NlKKEKEkEL sVFFtnSFSR  (95)
Consensus  LYGQSLGVHR IKTTPTTVKF -SPE-ILDKI N-KKEKE-DL RVL---SFSR CotC       NGNMSCnGFd ekeYsCNYIr TdTVnVIVDE enNeLNLFIG asFLsvqAqD  (148)
CooC       NGNMSCQGYT g.QnNCNYIK TnTVaVIVDD VENVLNLFIG NEFLaSgenD  (149)
CfaC       NGNMSCQGnT tiQYNCNYIK TksVdVIVDD VDNVvNLFIG NEFLdSeAhn  (145)
Consensus  NGNMSCQG-T --QYNCNYIK T-TV-VIVDD V-NVLNLFIG NEFL-S-A-D CotC       niYYQkniNs eKAFIHSQTI NFSESegYKs LSlkGvGAqG lTENSYlVFG  (198)
CooC       sDYYQpSkNt KKAFIHSQTI NLSDtGnYen LSIvGtGsLG ITDNSYAILG  (199)
CfaC       dEYhQlSrNv KKAFIqSQTI NLSDSGkYKr LSIsGnsALG ITDtSYAVLn  (195)
Consensus  --YYQ-S-N- KKAFIHSQTI NLSDSG-YK- LSI-G-GALG ITDNSYAVLG CotC       WdAiYNsSrk YtYknQSINn iYYRyDFDKk YYYQLGRMDR SDLSsaSSGN  (248)
CooC       WaANYNryks YnYNEQSINS LYFRHDFEKn FYYQLGRiDR SDLSQSSgGN  (249)
CfaC       WwmNYNkSng YsnNEktINS LYFRHDLDKr YYYQFGRMDR tDLSQSiSGs  (245)
Consensus  W-ANYN-S-- Y-YNEQSINS LYFRHDFDK- YYYQLGRMDR SDLSQSSSGN CotC       FNFNMLPLPD IDGfqiGTTQ SYIKNiEKSI sSPVTVMLTr FSRVEAFRNE  (298)
CooC       FNFdLLPvPD IyGmRaGTTQ SYIKNTgKSV ASPVTIMLTh FSRVEAYRNg  (299)
CfaC       FNFNLLPLPD IDGiRtGTTQ SYIKNTDKfI ASPVTVMLTn FSRVEAFRND  (295)
Consensus  FNFNLLPLPD IDG-R-GTTQ SYIKNT-KSI ASPVTVMLT- FSRVEAFRN- CotC       eLLGVWYLnS GINDLDTsRL PDGSYDLtLK IFEQDiLVRE EkVPFNKGGa  (348)
CooC       QLLGVWYLDa GIsELDTeRL PDGnYDLKLK IFEQEQLVRE EIVPFNKsGS  (349)
CfaC       QLLGVWYLDS GVNELDTaRL PyGSYDLKLK IFEntQLVRE EIIPFNKGrS  (345)
Consensus  QLLGVWYLDS GINELDT-RL PDGSYDLKLK IFEQ-QLVRE EIVPFNKGGS CotC       SfGDMQWDVF aQAGNIVNnN DsYIEKQtNk KtgINaGiRt PVTRNLSflQ  (398)
COOC       SIGDthWDVF VQAGdIINDN gRYVEKQkNH KSaINsGLRL PlTRNLaVQl  (399)
CfaC       SIGDMQWDIF VQgGNIVNDN DRYIEKQnNH KSsINtGLRL PITkNiSVQQ  (395)
Consensus  SIGDMQWDVF VQAGNIVNDN DRYIEKQ-NH KS-IN-GLRL P-TRNLSVQQ CotC       GGAIIDNdkY YEaGVnWrSG FLDGVLsgnF SFLYGDgArG NYQNISYTDG  (448)
CooC       GGAVIDNKnY YEtGIlWNSG LLDGSLNSkF tFLFGDdthG NYQNVSYTDG  (449)
CfaC       GvsVIDNKsY YEgslkWNSG iLsGSLNSeF SFLWGDnAkG NYQSISYTDG  (445)
Consensus  GGAVIDNK-Y YE-G---WNSG -LDGSLNS-F SFL-GD-A-G NYQNISYTDG CotC       FnLSFYrNDK sVDNCshNYs AGWSGCYESY SfSLSVPVsG WTtTLGYnhT  (498)
CooC       FSLSFYHNDK RVDdCGkdYN mGWSGCYESY SASLSIPVkG WnSTLaYSnT  (499)
CfaC       FSLSFYHNDK RVDNCGrNYN AGWSGCYESY SASLSIPllG WTSTLGYSdT  (495)
Consensus  FSLSFYHNDK RVDNCG-NYN AGWSGCYESY SASLSIPV-G WTSTLGYS-T CotC       nnEaVhKYDy tpEY..Ffsk kYKGvsKRWQ LTSSsSyKWM DYhViPTIGV  (546)
CooC       YStSVYrYDa vSEYvpY..y yYKGRTKRWQ LTaSTvvrWg DYNIMPTIGV  (547)
CfaC       YSESVYKshi lSEYgfYnqn iYKGRTqRWQ LTSSTSlKWM DYNfMPaIGI  (545)
Consensus  YSESVYKYD- -SEY--Y--- -YKGRTKRWQ LTSSTS-KWM DYN-MPTIGV CotC       YrSDQsrWsE qGGYFSLsFT RVkensaiNA GYSYNYvkhk nathEAFlDG  (596)
CooC       YNSEQkQWaD KGGYLSLTLT RVdggkSLNA GYSYNYSRGN YtSNDAFVEG  (597)
CfaC       YNSRQrQltD KGGYiSvTiT RasrenSLNt GYSYNYSRGN YsSNElFVDG  (595)
Consensus  YNSEQ-QW-D KGGY-SLT-T RV----SLNA GYSYNYSRGN Y-SNEAFVDG CotC       riT.TNtfgY sELGsRINtN knNTEaGVtG RVkNRFGDLN GSLNVNKSkt  (645)
CooC       hLvSdtNvSY rELsaRVsgN RyyTEGGVSG RINNRFGDLN GtLNVNKNRk  (647)
CfaC       yMTSTNNgdY hEaGmRfNkN RhNaEGRlSG RINNRFGDLN GSFSmNKNRn  (645)
Consensus  --TSTNN--Y -ELG-R-N-N R-NTEGGVSG RINNRFGDLN GSLNVNKNR-
```

TABLE 3-continued

Comparison of CooC, CotC and CfaC Protein Sequences[3]

```
CotC        SgkmTHSMsA  nYNSSFAiTg  DsVYWGGdAS  GLTKLSGGVV  nVrSdDksKE  (695)
CooC        ShdTTHSLTA  GYsSSFALTt  DGIYWGGSAS  GLTnLSGGIV  rVKSNEdesE  (697)
CfaC        tnsTnHSLTg  GYNSSFALTs  DGfYWGGSta  GLTKLaGGII  kVKSNDtkKn  (695)
Consensus   S--TTHSLTA  GYNSSFALT-  DG YWGGSAS  GLTKLSGGIV  -VKSND--KE CotC        LIKIsGSSYG  nYiLGSNDrs  FIPVsALMPs  nLTIEEiqsn  DKNItVqAls  (745)
CooC        LinVkGSSYG  hYSLGSNDsl  FIPVPALMqA  SLTIEENtnk  sKNIdVLAPT  (747)
CfaC        LVKVtGtlYG  dYSLGSNDna  FIPVPALtPA  SLiIEDNnyg  DnNIsILAPT  (745)
Consensus   L-KV-GSSYG  -YSLGSND--FIPVPALMPA  SLTIEEN---  DKNI-VLAPT CotC        KNDFFiLPGN  VFPIDVtANV  tVSYIGRaLD  dKGnPLSnAH  ILdvhgVrLD  (795)
CooC        KNtFFMLPGs  VYPIDVsANV  SftYVGRGvD  vKGrPLSGAy  ILNaqnIVLD  (797)
CfaC        nNDmFMLPGN  VYPVEIetkV  SVSYIGRGFD  pnGtPLSGAH  VLNephVILD  (795)
Consensus   KNDFFMLPGN  VYPIDV-ANV  SVSYIGRG-D  -KG-PLSGAH  ILN---V-LD CotC        EDGGFSFEtS  aqkKsLFLLK  DKdIYSCdvk  KyDLRsGVlF  tGDlICEhsg  (845)
CooC        EnGGFSFEsS  eNEKeLFLLK  DKTIYSCsLd  rsEMRnGIaF  VGEVaCnsti  (847)
CfaC        EDGGFSFEyt  gNEKtLFLLK  grTIYtCqLg  KnkvhkGlvF  VGDVICDins  (845)
Consensus   EDGGFSFE-S  -NEK-LFLLK  DKTIYSC-L-  K---R-GI-F  VGDVIC----

CotC        iErLgkDLVn  NPRVkqLLAY  k....                               (866)
CooC        kElLPEkLVt  NsRIhDLLAY  Nqdte                               (872)
CfaC        tssLPDEFVk  NPRVqDLLAk  Ndkg.                               (869)
Consensus   -E-LP--LV-  NPRV-DLLAY  N----
```

[3]Amino acid sequence comparison was done using the PILEUP algorithm in the GCG Software. The conserved amino acids are in upper Case letters; nonconserved amino acids are in lower case letters. Amino acids which are Conserved in all three proteins are given in bold-face letters in the consensus amino acid sequence

TABLE 4

Comparison of CooD, CotD and CfaE Protein Sequences[4]

```
CotD        LKKViFVLSM  FLcSq..vYg  qSwhtNvEaq  siNkTeSIGP  idrsaaaSyP  (48)
CooD        MKKIFifLSi  iFSa.....v  VSAgryPEtt  vgNLTkSfqa  prlDRsvqSP  (45)
CfaE        MnKILFIFtL  FFSSgfftFa  VSAdkNPgs.  .eNMTntIGP  h..DRggSSP  (46)
Consensus   MKKI-F-LS-  FFSS------  VSA--NPE--  --N-T-SIGP  ---DR--SSP CotD        ahyIFheHVA  GYNkdHSLFD  RMtFLCMSSt  daskGACPTg  EnSkss..qG  (96)
CooD        IYNIFtnHVA  GYslSHSLYD  RivFLCtSSs  NpNGACPTi  gtSGvqy..G  (93)
CfaE        IYNILnsylt  aYNgSHhLYD  RMsFLCLSSq  NtlNGACPss  DapGtatidG  (96)
Consensus   IYNIF--HVA  GYN-SHSLYD  RM-FLC-SS-  N--NGACPT-  --SG-----G CotD        ETNIkLiFTE  KkSLarktLN  LKGYKrFLYE  sdrCihYvdK  MnLNShtvkC  (146)
CooD        tTtITLQFTE  KRSLIKRniN  LaGnKkpiWE  NqsC.dFsnl  MvLNSksWsC  (142)
CfaE        ETNITLQFTE  KRSLIKReLq  iKGYKqFLFk  NanC...psK  LaLNSshFqC  (143)
Consensus   ETNITLQFTE  KRSLIKR-LN  LKGYK-FL-E  N--C-----K  M-LNS----C CotD        vg.sftrGvd  FtLYIPqGEI  dgLltGGIWE  ATLeLRVKRh  YDy...nhGT  (192)
CooD        qahgnAnGtl  LnLYIPAGEI  NKLPFGGIWE  ATLiLRlsRy  gEvssThYGn  (192)
CfaE        n.reqAsGat  LsLYIPAGEl  NKLPFGGVWn  AvLkLnVKRr  YD...TtYGT  (189)
Consensus   -----A-G--  L-LYIPAGEI  NKLPFGGIWE  ATL-LRVKR-  YD---T-YGT CotD        YkVNITVDLT  DKGNIQVWtP  kFHSdPRIDL  NLRPeGNGKY  SGSNvLEMCL  (242)
CooD        YTVNITVDLT  DKGNIQVWLP  gFHSNPRVDL  NLRPiGNyKY  SGSNSLDMCF  (242)
CfaE        YTINITVnLT  DKGNIQIWLP  qFkSNaRVDL  NLRPtGgGtY  iGrNSvDMCF  (239)
Consensus   YTVNITVDLT  DKGNIQVWLP  -FHSNPRVDL  NLRP-GNGKY  SGSNSLDMCF CotD        YDGYSThSqS  iEmRFQDDSq  TgnnEYNLiK  tGEplKkLPY  kLSLLLGGre  (292)
CooD        YDGYSTNSdS  MvIkFQDDNp  TnssEYNLyK  IGgteK.LPY  avSLLMGeKi  (291)
CfaE        YDGYSTNSsS  LEIRFQDDNs  ksdgkFyLkK  InDdsKeLvY  tLSLLLaGKn  (289)
Consensus   YDGYSTNS-S  -EIRFQDDN-  T---EYNL-K  IG---K-LPY  -LSLLLGGK- CotD        FYPnNGeAFT  INDtSsLfiN  WNRIksVsLP  qIsIPVLCWP  AnLtFmsElN  (342)
CooD        FYPvNGQsFT  INDsSvLETN  WNRVTAVaMP  EVnVPVLCWP  ARLlLnADVN  (341)
CfaE        LtPtNGQALn  INtaS.LETN  WNRITAVtMP  EISVPVLCWP  gRLqLdakVk  (338)
Consensus   FYP-NGQAFT  IND-S-LETN  WNRITAV-MP  EISVPVLCMP  ARL-L-A-VN CotD        aPDAGQYSGq  IyITFTPSSS  SL                                   (364)
CooD        NPEAGQYmGn  IkITFTPSSq  tL                                   (363)
CfaE        NPEAGeYSGi  lnVTFTPSSS  SL                                   (360)
Consensus   NPEAGQYSG-  I-ITFTPSSS  SL
```

TABLE 4-continued

Comparison of CooD, CotD and CfaE Protein Sequences[4]

[4]Amino acid sequence comparison was done using the PILEUP algorithm in the GCG SoftWare. The conserved amino acids are in upper case letters; nonconserved amino acids are in lower case letters. Amino acids which are conserved in all three proteins are given in bold-face letters in the consensus amino acid sequence.

---

We claim:

1. An isolated non-naturally occurring recombinant nucleic acid molecule comprising a sequence encoding CS2 pilin protein having an amino acid sequence as given in SEQ ID NO:3.

2. The nucleic acid molecule of claim 1 wherein said CS2 pilin-encoding sequence is as given in SEQ ID NO:1 from nucleotide 1255 through nucleotide 1764.

3. The nucleic acid molecule of claim 1 further comprising sequences encoding proteins having amino acid sequences as given in SEQ ID NO:2, SEQ ID NO:4 and SEQ ID NO:5.

4. The nucleic acid molecule of claim 3 wherein said further coding sequences are as given in SEQ ID NO:1 from nucleotide 499 to nucleotide 1212, from nucleotide 1836 to nucleotide 4433 and from nucleotide 4451 to nucleotide 5542.

5. The nucleic acid molecule of claim 3 wherein said molecule comprises a nucleotide sequence as given in SEQ ID NO:1, from nucleotide 499 to nucleotide 5698.

6. An enteric bacterial cell into which the non-naturally occurring nucleic acid molecule of claim 1 has been introduced.

7. An immunogenic composition comprising a DNA vaccine molecule capable of expressing at least one CS2-derived coding sequence in a human cell, wherein CS2-derived coding sequences encode proteins having amino acid sequences as given in SEQ ID NO:2: SEQ ID NO:3, amino acids 1 to 147: SEQ ID NO:4, amino acids 1 to 840: and SEQ ID NO:5.

8. The immunogenic composition of claim 7 wherein said vaccine DNA molecule is capable of expressing a protein with an amino acid sequence as given in SEQ ID NO:3 from amino acid 1 to amino acid 147.

9. The immunogenic composition of claim 7 wherein said vaccine DNA molecule is capable of expressing a protein with an amino acid sequence as given in SEQ ID NO:2 from amino acid 1 to amino acid 220.

10. The immunogenic composition of claim 7 wherein said vaccine DNA molecule is capable of expressing a protein with an amino acid sequence as given in SEQ ID NO:4 from amino acid 1 to amino acid 840.

11. The immunogenic composition of claim 7 wherein said vaccine DNA molecule is capable of expressing a protein with an amino acid sequence as given in SEQ ID NO:5 from amino acid 1 to amino acid 346.

12. An enteric bacterial cell into which the non-naturally occurring nucleic acid molecule of claim 3 has been introduced.

* * * * *

UNITED STATES PATENT AND TRADEMARK OFFICE
CERTIFICATE OF CORRECTION

PATENT NO. : 5,932,715            Page 1 of 2

DATED : August 3, 1999

INVENTOR(S) : Scott et al.

It is certified that error appears in the above-identified patent and that said Letters Patent is hereby corrected as shown below:

On the Title Page, under [75], please delete "Morris Plains, N.J." and replace with --Westwood, MA--.
In Column 7, line 43, please delete "NO:$1$" and replace with --NO:1--. (No italics)
In Column 8, line 58, please delete "CS1 and CS1" and replace with --CS1 and CS2--.
In Column 9, line 17, please delete "NO:13," and replace with --NO:3,".
In Column 13, line 6, please delete "an" and replace with --a--.
In Column 17, line 34, please delete "pe" and replace with --be--.
In Column 19/20, Table 1, third line (CotB), second set, please rewrite "YFESVKPggQ" as
    --YFESVKPgqQ--.
In Column 19/20, Table 1, fifth line (CfaA), third set, please rewrite "EnV.idNKKL" as --EnV.idNKkL--.
In Column 19/20, Table 1, eighth line (CooB), fourth set , please rewrite "FFCKkTSINn" as
    --FFCKkTSInN--.
In Column 19/20, Table 1, 14$^{th}$ line (Consensus), first set, please rewrite "NITP--SFDT" as --NIyP--SFDT--.
In Column 19/20, Table 2, seventh line (CfaB), fourth set, please rewrite "VIVKLa.Dtp" as --VIVKLa.DtP--.
In Column 21/22, Table 3, first line (CotC), first set, please rewrite "M. .rafNKIt" as --M..rafNKIt--.
In Column 21/22, Table 3, first line (CotC), second set, please rewrite "VfIlfiPGlC" as --VfIlfipGlC--.
In Column 21/22, Table 3, second line (CooC), second set, please rewrite "IvlSVliGsS" as --IvlSVliGss--.
In Column 21/22, Table 3, second line (CooC), third set, please rewrite "sGfaBkynlv" as --sGfaskynlv--.
In Column 21/22, Table 3, 30$^{th}$ line, row indicator "COOC" should be --CooC--.
In Column 21/22, Table 3, 47$^{th}$ line (CfaC), first set, please rewrite "YNSRQrQltD" as --YNSEQrQltD--.
In Column 21/22, Table 3, 49$^{th}$ line (CotC), fifth set, please rewrite "GSLNVNKSkt" as --GSLNVNKskt--.
In Column 21/22, Table 3, 50$^{th}$ line (CooC), first set, please rewrite "hLvSdtNvSY" as --hLvSdtNvsY--.
In Column 23/24, Table 3, fourth line (Consensus), third set, please rewrite "DG YWGGSAS" as
    --DG-YWGGSAS--.
In Column 23/24, Table 3, sixth line (CooC), first set, please rewrite "LinVkGSSYG" as --LlnVkGSSYG--.
In Column 23/24, Table 3, eighth line (Consensus), between the second and third set, please insert a space
    between sets.
In Column 23/24, Table 3 footnote, in the second line, please delete "Case" and replace with --case--.
In Column 23/24, Table 3 footnote, in the fourth line, please delete "Conserved" and replace with
    --conserved--.

UNITED STATES PATENT AND TRADEMARK OFFICE
CERTIFICATE OF CORRECTION

PATENT NO. : 5,932,715

DATED : August 3, 1999

INVENTOR(S) : Scott et al.

It is certified that error appears in the above-identified patent and that said Letters Patent is hereby corrected as shown below:

In Column 23/24, Table 3 footnote, in the fifth line, please insert a period after "sequence".
In Column 23/24, Table 4, sixth line (CooD), fourth set, please rewrite "NpNGACPTi" as --NpvNGACPTi--.
In Column 23/24, Table 4, 21$^{st}$ line (CotD), second set, please rewrite "iEmRFQDDSq" as --iEmRFQDDsq--.
In Column 23/24, Table 4, 25$^{th}$ line (CotD), fourth set, please rewrite "qIsIPVLCWP" as --qISIPVLCWP--.
In Column 23/24, Table 4, 27$^{th}$ line (CfaE), fifth set, please rewrite "gRLqLdakVk" as --gRLqLdAkVk--.
In Column 23/24, Table 4, 28$^{th}$ line (Consensus), fourth set, please rewrite "EISVPVLCMP" as
 --EISVPVLCWP--.
In Column 25/26, Table 4 footnote, in the second line, please delete "SoftWare" and replace with
 --Software--.

Signed and Sealed this

First Day of February, 2000

Attest:

Attesting Officer

Q. TODD DICKINSON

Acting Commissioner of Patents and Trademarks

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 5798 base pairs
      (B) TYPE: nucleic acid
      (C) STRANDEDNESS: double
      (D) TOPOLOGY: circular (ii) MOLECULE TYPE: DNA (genomic)

(iii) HYPOTHETICAL: NO (iv) ANTI-SENSE: NO (vi) ORIGINAL SOURCE:
      (A) ORGANISM: Escherichia coli (ix) FEATURE:
      (A) NAME/KEY: CDS
      (B) LOCATION: 499..1215

(ix) FEATURE:
      (A) NAME/KEY: sig_peptide
      (B) LOCATION: 499..552

(ix) FEATURE:
      (A) NAME/KEY: mat_peptide
      (B) LOCATION: 553..1212

(ix) FEATURE:
      (A) NAME/KEY: CDS
      (B) LOCATION: 1255..1767

(ix) FEATURE:
      (A) NAME/KEY: sig_peptide
      (B) LOCATION: 1255..1323

(ix) FEATURE:
      (A) NAME/KEY: mat_peptide
      (B) LOCATION: 1324..1764

(ix) FEATURE:
      (A) NAME/KEY: CDS
      (B) LOCATION: 1836..4436

(ix) FEATURE:
      (A) NAME/KEY: sig_peptide
      (B) LOCATION: 1836..1913

(ix) FEATURE:
      (A) NAME/KEY: mat_peptide
      (B) LOCATION: 1914..4433

(ix) FEATURE:
      (A) NAME/KEY: CDS
      (B) LOCATION: 4451..5545

(ix) FEATURE:
      (A) NAME/KEY: sig_peptide
      (B) LOCATION: 4451..4504

-continued (ix) FEATURE:
    (A) NAME/KEY: mat_peptide
    (B) LOCATION: 4505..5542

(xi) SEQUENCE DESCRIPTION: SEQ ID NO:1:

```
CTGCAGATGG CGCTGTGGCG GCGTAAGAGG CCCCGGAACG TTATCGTTCA CACGGACCGT      60

GGAGGCCAGT ACTGTTCAGC AGATTATCAG GCGCAACTGA AGCGGCATAA TCTGCGTGGA     120

AGTATGAGCG CAAAAGGTTG CTGCTACGAT AATGCCTGCG TGGAAAGCTT CTTTCATTCG     180

CTGAAAGTGG AATGTATCCA TGGAGAACAC TTTATGAGCC GGGAAATAAG TCGGGCAACG     240

GTGTTTAATT ATATCGAATG TGATTACAAT CGGTGGCGGC GGCACAGTTG GTGTGGCGGC     300

CTCAGTCCGG AACAATTTGA AAACAAGAAC CTCGCTTAGG CCTGTGTCCA TATTACGTGG     360

GTAGGATCAA AACACTATCA ATAAGTTGGA GTCATTACCG GCATTCTTGA AAGCCTCATG     420

CGTGACAGGG TGTGTGTTGT ATTTTTATCA TATTTTAACG CCTGCTTTCT GATAATGTTT     480

AGGAAAGGGG TGATATGT ATG AAG ATA TTG TTA TTT GTT ATT CTG TTT TTT      531
              Met Lys Ile Leu Leu Phe Val Ile Leu Phe Phe
              -18         -15                 -10

AAT GTT TTT GCT GCC AGT GCA AAT TTT ATG GTA TAT CCG ATC TCA AAG       579
Asn Val Phe Ala Ala Ser Ala Asn Phe Met Val Tyr Pro Ile Ser Lys
       -5                  1                   5

GAT ATA CAG AGT GGT GGC AGC GAA ACT ATA AAA GTT TTT TCA AAA TCT       627
Asp Ile Gln Ser Gly Gly Ser Glu Thr Ile Lys Val Phe Ser Lys Ser
10                  15                  20                  25

AAA GAT GTT CAG TAT ATA AAG ATA TAT ACG AAA AGG GTT ATT AAT CCA       675
Lys Asp Val Gln Tyr Ile Lys Ile Tyr Thr Lys Arg Val Ile Asn Pro
                30                  35                  40

GGA ACA AAA GAA GAG CAA GAG GTT GAT ATA AAA AAT TGG GAT GGA GGT       723
Gly Thr Lys Glu Glu Gln Glu Val Asp Ile Lys Asn Trp Asp Gly Gly
            45                  50                  55

CTG ATT GTA ACT CCG GCA AAA GTT GTT TTG CCA GCT GGA GCA AGT AAG       771
Leu Ile Val Thr Pro Ala Lys Val Val Leu Pro Ala Gly Ala Ser Lys
        60                  65                  70

TCA ATA CGA CTT ACT GAG ATA AAT AAA AAA GAG CAG GAG GAA GTC TAT       819
Ser Ile Arg Leu Thr Glu Ile Asn Lys Lys Glu Gln Glu Glu Val Tyr
    75                  80                  85

CGT GTG TAT TTT GAA TCT GTA AAA CCG GGA CAG CAA GAT GAT ATA GAG       867
Arg Val Tyr Phe Glu Ser Val Lys Pro Gly Gln Gln Asp Asp Ile Glu
90                  95                 100                 105

GAA AAA AAT GGG CGT GTA AAT ACT GAT TTA TCA GTA AAC ATA ATC TAT       915
Glu Lys Asn Gly Arg Val Asn Thr Asp Leu Ser Val Asn Ile Ile Tyr
                110                 115                 120

GCC GCT CTC ATA AGA ACC AGC CCT GAG AAC CCA CAG AGG AAA CTT GAT       963
Ala Ala Leu Ile Arg Thr Ser Pro Glu Asn Pro Gln Arg Lys Leu Asp
            125                 130                 135

GTA TCC ATA GAA TCA AAC AAT GTA TGG ATT AAG AAC ACT GGA AAT ATT      1011
Val Ser Ile Glu Ser Asn Asn Val Trp Ile Lys Asn Thr Gly Asn Ile
        140                 145                 150

AGG CTG GGA ATT AAG GAT GTA TTC TTG TGT GAT ACA ACC AGC ATA AAT      1059
Arg Leu Gly Ile Lys Asp Val Phe Leu Cys Asp Thr Thr Ser Ile Asn
    155                 160                 165

GAT AAA TGT GCA AAG TTT TCT TAT AAT AGA AAT CTA TAT CCA GAT ATG      1107
Asp Lys Cys Ala Lys Phe Ser Tyr Asn Arg Asn Leu Tyr Pro Asp Met
170                 175                 180                 185

TCG GTA GAT ACT AAA TTA GGA AAA AAA GGA TTT TCT TAT GCT GTC ATT      1155
Ser Val Asp Thr Lys Leu Gly Lys Lys Gly Phe Ser Tyr Ala Val Ile
                190                 195                 200

GAT ACA AAG GAT GAC AGA AAT GAA AAT AGC GGA GAG TTA ATT AAC ATA      1203
Asp Thr Lys Asp Asp Arg Asn Glu Asn Ser Gly Glu Leu Ile Asn Ile
```

```
                    205              210             215
AAG CTC CCG TAA GATAAATTGT TCAATAACCA CTGTATAAGG GTGTAAATA ATG     1257
Lys Leu Pro  *                                              Met
        220                                                 -23

AAA CTC AAT AAG ATT ATT GGA GCA TTA GTT CTT TCA TCT ACA TTT GTT   1305
Lys Leu Asn Lys Ile Ile Gly Ala Leu Val Leu Ser Ser Thr Phe Val
            -20             -15             -10

AGC ATG GGG GCT TCT GCT GCC GAG AAA AAT ATC ACT GTA ACT GCT AGC   1353
Ser Met Gly Ala Ser Ala Ala Glu Lys Asn Ile Thr Val Thr Ala Ser
     -5              1               5                       10

GTT GAT CCA ACT ATC GAT CTG ATG CAA TCT GAT GGC ACA GCG TTA CCA   1401
Val Asp Pro Thr Ile Asp Leu Met Gln Ser Asp Gly Thr Ala Leu Pro
                15              20              25

AGT GCA GTT AAT ATT GCA TAT CTT CCA GGA GAG AAA AGA TTT GAA TCT   1449
Ser Ala Val Asn Ile Ala Tyr Leu Pro Gly Glu Lys Arg Phe Glu Ser
             30              35              40

GCT CGT ATC AAT ACC CAA GTT CAT ACC AAT AAT AAA ACT AAG GGT ATT   1497
Ala Arg Ile Asn Thr Gln Val His Thr Asn Asn Lys Thr Lys Gly Ile
         45              50              55

CAG ATA AAG CTT ACT AAT GAT AAT GTG GTA ATG ACT AAC TTA TCT GAT   1545
Gln Ile Lys Leu Thr Asn Asp Asn Val Val Met Thr Asn Leu Ser Asp
 60              65              70

CCA AGC AAG ACT ATT CCT TTA GAG GTT TCA TTC GCT GGC ACT AAG CTG   1593
Pro Ser Lys Thr Ile Pro Leu Glu Val Ser Phe Ala Gly Thr Lys Leu
 75              80              85                       90

AGC ACA GCT GCA ACA TCT ATT ACT GCC GAT CAA TTA AAT TTT GGC GCA   1641
Ser Thr Ala Ala Thr Ser Ile Thr Ala Asp Gln Leu Asn Phe Gly Ala
                 95              100             105

GCT GGT GTA GAG ACA GTT TCT GCA ACT AAG GAA CTC GTT ATT AAT GCA   1689
Ala Gly Val Glu Thr Val Ser Ala Thr Lys Glu Leu Val Ile Asn Ala
            110             115             120

GGA AGC ACC CAG CAA ACT AAT ATT GTA GCT GGT AAC TAT CAA GGA TTG   1737
Gly Ser Thr Gln Gln Thr Asn Ile Val Ala Gly Asn Tyr Gln Gly Leu
        125             130             135

GTG TCA ATT GTG CTT ACT CAA GAA CCT TAA TAAACATTAA GATATATCAA     1787
Val Ser Ile Val Leu Thr Gln Glu Pro  *
    140             145

CAGGGTTGCT GATTTTTTAG TCACCCTGTT ATTAAGAAA ATATATTT ATG CGA GCT   1844
                                                    Met Arg Ala
                                                    -26 -25

TTC AAT AAA ATA ACT GTT TCA ATT TTG TTT ATT CCT GGT TTA TGT TTT  1892
Phe Asn Lys Ile Thr Val Phe Ile Leu Phe Ile Pro Gly Leu Cys Phe
            -20             -15             -10

GGA ACG AAT GGT TTA GAG AGT AAA AAA AAT ATT CCT GAA GAA TTT ATA  1940
Gly Thr Asn Gly Leu Glu Ser Lys Lys Asn Ile Pro Glu Glu Phe Ile
     -5              1               5

GAC TTA TGG ATG GAA CAG GAT GAA TTA CTT GAA GTT AAT TTA TAT GGG  1988
Asp Leu Trp Met Glu Gln Asp Glu Leu Leu Glu Val Asn Leu Tyr Gly
 10              15              20              25

CGT TCT CTA GGT GTT CAT CGT GTA TTG ACA ACG CCT ACT ACT GTG AAA  2036
Arg Ser Leu Gly Val His Arg Val Leu Thr Thr Pro Thr Thr Val Lys
             30              35              40

TTT TCA TCT GTA GAG GAA ATT CTA GAA AAG ATT AAT GTG AAA CAA GAG  2084
Phe Ser Ser Val Glu Glu Ile Leu Glu Lys Ile Asn Val Lys Gln Glu
             45              50              55

AAA AAA GAA GAC CTG AGA AGT CTT CTT CTT CAA TCA TAT TCC CGC AAC  2132
Lys Lys Glu Asp Leu Arg Ser Leu Leu Leu Gln Ser Tyr Ser Arg Asn
         60              65              70

GGG AAT ATG AGT TGT AAT GGG TTT GAT GAA AAG GAA TAT AGC TGC AAT  2180
Gly Asn Met Ser Cys Asn Gly Phe Asp Glu Lys Glu Tyr Ser Cys Asn
```

-continued

|  |  |  |  |
|---|---|---|---|
| | 75 | 80 | 85 |
| TAC ATT AGA ACT GAT ACG GTT AAT GTT ATT GTA GAT GAA GAA AAT AAT | 2228 |
| Tyr Ile Arg Thr Asp Thr Val Asn Val Ile Val Asp Glu Glu Asn Asn |  |
| 90 95 100 105 |  |
| GAG CTA AAT CTT TTT ATA GGT GCG AGT TTT CTT TCT GTT CAA GCT CAG | 2276 |
| Glu Leu Asn Leu Phe Ile Gly Ala Ser Phe Leu Ser Val Gln Ala Gln |  |
| 110 115 120 |  |
| GAT AAT ATT TAT TAT CAA AAA AAT ATA AAC TCA GAA AAA GCA TTC ATT | 2324 |
| Asp Asn Ile Tyr Tyr Gln Lys Asn Ile Asn Ser Glu Lys Ala Phe Ile |  |
| 125 130 135 |  |
| CAC AGT CAG ACA ATT AAC TTT TCT GAA TCT GAA GGG TAT AAA AGT TTA | 2372 |
| His Ser Gln Thr Ile Asn Phe Ser Glu Ser Glu Gly Tyr Lys Ser Leu |  |
| 140 145 150 |  |
| TCT TTG AAA GGG GTT GGT GCA CAG GGG TTA ACT GAA AAT AGT TAT CTT | 2420 |
| Ser Leu Lys Gly Val Gly Ala Gln Gly Leu Thr Glu Asn Ser Tyr Leu |  |
| 155 160 165 |  |
| GTT TTT GGT TGG GAT GCC ATA TAT AAT AGT TCT AGG AAA TAC ACA TAT | 2468 |
| Val Phe Gly Trp Asp Ala Ile Tyr Asn Ser Ser Arg Lys Tyr Thr Tyr |  |
| 170 175 180 185 |  |
| AAA AAT CAG TCA ATC AAT AAT ATA TAT TAC AGA TAT GAT TTT GAT AAA | 2516 |
| Lys Asn Gln Ser Ile Asn Asn Ile Tyr Tyr Arg Tyr Asp Phe Asp Lys |  |
| 190 195 200 |  |
| AAA TAT TAT TAT CAG TTG GGG CGA ATG GAT CGT TCA GAT TTA TCA AGT | 2564 |
| Lys Tyr Tyr Tyr Gln Leu Gly Arg Met Asp Arg Ser Asp Leu Ser Ser |  |
| 205 210 215 |  |
| GCC TCT AGT GGT AAT TTT AAT TTC AAT ATG CTT CCT TTG CCT GAT ATT | 2612 |
| Ala Ser Ser Gly Asn Phe Asn Phe Asn Met Leu Pro Leu Pro Asp Ile |  |
| 220 225 230 |  |
| GAT GGA TTT CAG ATA GGT ACG ACC CAA TCC TAT ATT AAA AAT ATC GAA | 2660 |
| Asp Gly Phe Gln Ile Gly Thr Thr Gln Ser Tyr Ile Lys Asn Ile Glu |  |
| 235 240 245 |  |
| AAA TCA ATA TCA TCG CCA GTA ACC GTT ATG TTA ACC CGA TTT TCT AGG | 2708 |
| Lys Ser Ile Ser Ser Pro Val Thr Val Met Leu Thr Arg Phe Ser Arg |  |
| 250 255 260 265 |  |
| GTT GAA GCC TTT CGT AAT GAA GAG TTA CTG GGA GTA TGG TAT TTG AAT | 2756 |
| Val Glu Ala Phe Arg Asn Glu Glu Leu Leu Gly Val Trp Tyr Leu Asn |  |
| 270 275 280 |  |
| TCA GGA ATC AAT GAT CTC GAT ACA AGT CGT TTG CCT GAC GGC AGT TAT | 2804 |
| Ser Gly Ile Asn Asp Leu Asp Thr Ser Arg Leu Pro Asp Gly Ser Tyr |  |
| 285 290 295 |  |
| GAT TTA ACG TTG AAG ATA TTT GAG CAG GAC ATT CTT GTT CGT GAA GAG | 2852 |
| Asp Leu Thr Leu Lys Ile Phe Glu Gln Asp Ile Leu Val Arg Glu Glu |  |
| 300 305 310 |  |
| AAG GTC CCT TTT AAC AAG GGA GGA GCC TCT TTT GGG GAT ATG CAA TGG | 2900 |
| Lys Val Pro Phe Asn Lys Gly Gly Ala Ser Phe Gly Asp Met Gln Trp |  |
| 315 320 325 |  |
| GAT GTG TTT GCT CAG GCT GGT AAT ATT GTC AAT AAT AAC GAT AGT TAT | 2948 |
| Asp Val Phe Ala Gln Ala Gly Asn Ile Val Asn Asn Asn Asp Ser Tyr |  |
| 330 335 340 345 |  |
| ATT GAG AAG CAA ACT AAT AAA AAA ACG GGA ATA AAT GCT GGT ATA CGT | 2996 |
| Ile Glu Lys Gln Thr Asn Lys Lys Thr Gly Ile Asn Ala Gly Ile Arg |  |
| 350 355 360 |  |
| ACG CCT GTA ACC AGA AAT TTA TCG TTC TTA CAG GGC GGT GCT ATA ATT | 3044 |
| Thr Pro Val Thr Arg Asn Leu Ser Phe Leu Gln Gly Gly Ala Ile Ile |  |
| 365 370 375 |  |
| GAT AAT GAT AAA TAT TAT GAG GCT GGT GTT AAC TGG CGT TCA GGG TTT | 3092 |
| Asp Asn Asp Lys Tyr Tyr Glu Ala Gly Val Asn Trp Arg Ser Gly Phe |  |
| 380 385 390 |  |
| CTT GAT GGG GTA CTA AGT GGA AAC TTC AGT TTC CTG TAT GGT GAT GGT | 3140 |
| Leu Asp Gly Val Leu Ser Gly Asn Phe Ser Phe Leu Tyr Gly Asp Gly |  |

-continued

| | | | | | | | | | | | | |
|---|---|---|---|---|---|---|---|---|---|---|---|---|
| | 395 | | | 400 | | | | 405 | | | | |
| GCA | AGA | GGA | AAT | TAT | CAA | AAT | ATT | TCG | TAT | ACC | GAT | GGT | TTT | AAT | CTC | 3188 |
| Ala | Arg | Gly | Asn | Tyr | Gln | Asn | Ile | Ser | Tyr | Thr | Asp | Gly | Phe | Asn | Leu | |
| 410 | | | | | 415 | | | | | 420 | | | | | 425 | |
| TCT | TTT | TAT | CGT | AAT | GAT | AAA | AGC | GTT | GAT | AAT | TGT | AGT | CAC | AAT | TAC | 3236 |
| Ser | Phe | Tyr | Arg | Asn | Asp | Lys | Ser | Val | Asp | Asn | Cys | Ser | His | Asn | Tyr | |
| | | | | 430 | | | | | 435 | | | | | 440 | | |
| AGT | GCG | GGA | TGG | AGT | GGG | TGC | TAT | GAG | TCT | TAT | TCC | TTT | TCA | CTA | AGT | 3284 |
| Ser | Ala | Gly | Trp | Ser | Gly | Cys | Tyr | Glu | Ser | Tyr | Ser | Phe | Ser | Leu | Ser | |
| | | | | 445 | | | | | 450 | | | | | 455 | | |
| GTT | CCT | GTA | TCT | GGC | TGG | ACT | ACT | ACT | CTT | GGC | TAT | AAC | CAT | ACA | AAT | 3332 |
| Val | Pro | Val | Ser | Gly | Trp | Thr | Thr | Thr | Leu | Gly | Tyr | Asn | His | Thr | Asn | |
| | | | 460 | | | | | 465 | | | | | 470 | | | |
| AAT | GAG | GCT | GTA | CAT | AAA | TAT | GAT | TAC | ACC | CCG | GAA | TAT | TTT | TTT | AGT | 3380 |
| Asn | Glu | Ala | Val | His | Lys | Tyr | Asp | Tyr | Thr | Pro | Glu | Tyr | Phe | Phe | Ser | |
| 475 | | | | | 480 | | | | | 485 | | | | | | |
| AAA | AAA | TAT | AAA | GGT | GTC | AGT | AAA | AGA | TGG | CAA | TTG | ACA | TCT | TCT | TCG | 3428 |
| Lys | Lys | Tyr | Lys | Gly | Val | Ser | Lys | Arg | Trp | Gln | Leu | Thr | Ser | Ser | Ser | |
| 490 | | | | | 495 | | | | | 500 | | | | | 505 | |
| TCC | TAT | AAA | TGG | ATG | GAT | TAT | CAT | GTG | ATT | CCG | ACG | ATA | GGT | GTA | TAT | 3476 |
| Ser | Tyr | Lys | Trp | Met | Asp | Tyr | His | Val | Ile | Pro | Thr | Ile | Gly | Val | Tyr | |
| | | | | 510 | | | | | 515 | | | | | 520 | | |
| CGT | AGT | GAT | CAG | AGT | CGA | TGG | AGT | GAG | CAG | GGA | GGG | TAT | TTT | TCT | TTG | 3524 |
| Arg | Ser | Asp | Gln | Ser | Arg | Trp | Ser | Glu | Gln | Gly | Gly | Tyr | Phe | Ser | Leu | |
| | | | | 525 | | | | | 530 | | | | | 535 | | |
| AGT | TTT | ACC | CGA | GTA | AAG | GAA | AAT | AGT | GCC | ATT | AAT | GCA | GGA | TAT | TCT | 3572 |
| Ser | Phe | Thr | Arg | Val | Lys | Glu | Asn | Ser | Ala | Ile | Asn | Ala | Gly | Tyr | Ser | |
| | | | 540 | | | | | 545 | | | | | 550 | | | |
| TAT | AAT | TAT | GTA | AAG | CAT | AAA | AAT | GCC | ACA | CAT | GAG | GCT | TTT | TTA | GAT | 3620 |
| Tyr | Asn | Tyr | Val | Lys | His | Lys | Asn | Ala | Thr | His | Glu | Ala | Phe | Leu | Asp | |
| 555 | | | | | 560 | | | | | 565 | | | | | | |
| GGT | CGT | ATA | ACG | ACA | AAT | ACT | TTT | GGC | TAT | AGT | GAA | TTA | GGC | TCT | CGT | 3668 |
| Gly | Arg | Ile | Thr | Thr | Asn | Thr | Phe | Gly | Tyr | Ser | Glu | Leu | Gly | Ser | Arg | |
| 570 | | | | | 575 | | | | | 580 | | | | | 585 | |
| ATA | AAT | ACG | AAC | AAA | AAT | AAC | ACA | GAA | GCA | GGT | GTT | ACC | GGA | CGT | GTA | 3716 |
| Ile | Asn | Thr | Asn | Lys | Asn | Asn | Thr | Glu | Ala | Gly | Val | Thr | Gly | Arg | Val | |
| | | | | 590 | | | | | 595 | | | | | 600 | | |
| AAA | AAC | AGG | TTT | GGA | GAT | CTG | AAT | GGT | TCA | TTA | AAT | GTT | AAT | AAA | AGT | 3764 |
| Lys | Asn | Arg | Phe | Gly | Asp | Leu | Asn | Gly | Ser | Leu | Asn | Val | Asn | Lys | Ser | |
| | | | 605 | | | | | 610 | | | | | 615 | | | |
| AAA | ACA | TCC | GGT | AAG | ATG | ACT | CAC | TCA | ATG | AGT | GCA | AAC | TAT | AAC | TCC | 3812 |
| Lys | Thr | Ser | Gly | Lys | Met | Thr | His | Ser | Met | Ser | Ala | Asn | Tyr | Asn | Ser | |
| | | | 620 | | | | | 625 | | | | | 630 | | | |
| TCA | TTT | GCA | ATT | ACT | GGT | GAT | TCT | GTC | TAT | TGG | GGG | GGA | GAT | GCC | TCT | 3860 |
| Ser | Phe | Ala | Ile | Thr | Gly | Asp | Ser | Val | Tyr | Trp | Gly | Gly | Asp | Ala | Ser | |
| | | 635 | | | | | 640 | | | | | 645 | | | | |
| GGT | TTA | ACG | AAG | CTA | TCT | GGG | GGT | GTG | GTG | AAT | GTA | AGA | TCA | GAT | GAT | 3908 |
| Gly | Leu | Thr | Lys | Leu | Ser | Gly | Gly | Val | Val | Asn | Val | Arg | Ser | Asp | Asp | |
| 650 | | | | | 655 | | | | | 660 | | | | | 665 | |
| AAA | TCA | AAA | GAG | CTA | ATA | AAA | ATA | TCA | GGT | TCT | TCA | TAT | GGT | AAT | TAT | 3956 |
| Lys | Ser | Lys | Glu | Leu | Ile | Lys | Ile | Ser | Gly | Ser | Ser | Tyr | Gly | Asn | Tyr | |
| | | | | 670 | | | | | 675 | | | | | 680 | | |
| ATC | CTC | GGC | AGT | AAT | GAC | CGT | TCA | TTT | ATC | CCT | GTA | AGT | GCA | TTA | ATG | 4004 |
| Ile | Leu | Gly | Ser | Asn | Asp | Arg | Ser | Phe | Ile | Pro | Val | Ser | Ala | Leu | Met | |
| | | 685 | | | | | 690 | | | | | 695 | | | | |
| CCA | AGT | AAC | CTA | ACT | ATA | GAA | GAG | ATT | CAG | TCA | AAC | GAC | AAG | AAT | ATT | 4052 |
| Pro | Ser | Asn | Leu | Thr | Ile | Glu | Glu | Ile | Gln | Ser | Asn | Asp | Lys | Asn | Ile | |
| | | 700 | | | | | 705 | | | | | 710 | | | | |
| ACT | GTT | CAG | GCG | TTA | TCA | AAA | AAT | GAC | TTT | TTT | ATT | CTG | CCT | GGT | AAT | 4100 |
| Thr | Val | Gln | Ala | Leu | Ser | Lys | Asn | Asp | Phe | Phe | Ile | Leu | Pro | Gly | Asn | |

-continued

| | | | | | | | | | | | | | | | | |
|---|---|---|---|---|---|---|---|---|---|---|---|---|---|---|---|---|
| | 715 | | | | 720 | | | | | 725 | | | | | | |
| GTT | TTC | CCT | ATT | GAT | GTA | ACT | GCT | AAT | GTG | ACA | GTT | TCT | TAT | ATA | GGG | 4148 |
| Val | Phe | Pro | Ile | Asp | Val | Thr | Ala | Asn | Val | Thr | Val | Ser | Tyr | Ile | Gly | |
| 730 | | | | 735 | | | | | 740 | | | | | | 745 | |
| AGA | GCT | CTT | GAT | GAT | AAA | GGA | AAT | CCA | TTA | TCA | AAT | GCC | CAT | ATA | CTT | 4196 |
| Arg | Ala | Leu | Asp | Asp | Lys | Gly | Asn | Pro | Leu | Ser | Asn | Ala | His | Ile | Leu | |
| | | | | 750 | | | | | 755 | | | | | 760 | | |
| GAT | GTT | CAC | GGG | GTT | AGG | CTG | GAT | GAG | GAT | GGT | GGT | TTT | TCT | TTC | GAA | 4244 |
| Asp | Val | His | Gly | Val | Arg | Leu | Asp | Glu | Asp | Gly | Gly | Phe | Ser | Phe | Glu | |
| | | | 765 | | | | | 770 | | | | | 775 | | | |
| ACT | TCA | GCT | CAA | AAG | AAA | TCT | CTT | TTC | CTG | TTA | AAA | GAT | AAA | GAT | ATT | 4292 |
| Thr | Ser | Ala | Gln | Lys | Lys | Ser | Leu | Phe | Leu | Leu | Lys | Asp | Lys | Asp | Ile | |
| | | | 780 | | | | 785 | | | | | 790 | | | | |
| TAT | TCA | TGT | GAT | GTT | AAG | AAA | TAT | GAT | TTA | CGT | AGT | GGT | GTT | TTA | TTT | 4340 |
| Tyr | Ser | Cys | Asp | Val | Lys | Lys | Tyr | Asp | Leu | Arg | Ser | Gly | Val | Leu | Phe | |
| | 795 | | | | | 800 | | | | | 805 | | | | | |
| ACT | GGT | GAC | CTT | ATA | TGT | GAA | CAC | AGT | GGT | ATA | GAA | CGT | CTT | GGA | AAA | 4388 |
| Thr | Gly | Asp | Leu | Ile | Cys | Glu | His | Ser | Gly | Ile | Glu | Arg | Leu | Gly | Lys | |
| 810 | | | | | 815 | | | | | 820 | | | | | 825 | |
| GAT | TTG | GTT | AAC | AAT | CCA | AGA | GTT | AAG | CAA | CTG | CTT | GCT | TAT | AAA | TAA | 4436 |
| Asp | Leu | Val | Asn | Asn | Pro | Arg | Val | Lys | Gln | Leu | Leu | Ala | Tyr | Lys | * | |
| | | | | 830 | | | | | 835 | | | | | 840 | | |
| CCAAGAGGTG | AACT | TTG | AAA | AAA | GTG | ATT | TTT | GTT | TTA | TCC | ATG | TTT | CTA | | | 4486 |
| | | Leu | Lys | Lys | Val | Ile | Phe | Val | Leu | Ser | Met | Phe | Leu | | | |
| | | -18 | | | -15 | | | | | -10 | | | | | | |
| TGT | TCT | CAG | GTT | TAC | GGG | CAA | TCA | TGG | CAT | ACG | AAC | GTA | GAG | GCT | GGT | 4534 |
| Cys | Ser | Gln | Val | Tyr | Gly | Gln | Ser | Trp | His | Thr | Asn | Val | Glu | Ala | Gly | |
| | -5 | | | | 1 | | | | 5 | | | | | | 10 | |
| TCA | ATA | AAT | AAA | ACA | GAG | TCG | ATA | GGC | CCC | ATA | GAC | CGA | AGT | GCT | GCT | 4582 |
| Ser | Ile | Asn | Lys | Thr | Glu | Ser | Ile | Gly | Pro | Ile | Asp | Arg | Ser | Ala | Ala | |
| | | | | 15 | | | | | 20 | | | | | 25 | | |
| GCA | TCG | TAT | CCT | GCT | CAT | TAT | ATA | TTT | CAT | GAA | CAT | GTT | GCT | GGT | TAC | 4630 |
| Ala | Ser | Tyr | Pro | Ala | His | Tyr | Ile | Phe | His | Glu | His | Val | Ala | Gly | Tyr | |
| | | | 30 | | | | 35 | | | | | 40 | | | | |
| AAT | AAA | GAT | CAC | TCT | CTT | TTT | GAC | AGG | ATG | ACG | TTT | TTA | TGT | ATG | TCA | 4678 |
| Asn | Lys | Asp | His | Ser | Leu | Phe | Asp | Arg | Met | Thr | Phe | Leu | Cys | Met | Ser | |
| | | 45 | | | | 50 | | | | | 55 | | | | | |
| TCA | ACA | GAT | GCA | TCT | AAA | GGT | GCA | TGT | CCG | ACA | GGA | GAA | AAC | TCC | AAA | 4726 |
| Ser | Thr | Asp | Ala | Ser | Lys | Gly | Ala | Cys | Pro | Thr | Gly | Glu | Asn | Ser | Lys | |
| | 60 | | | | 65 | | | | | 70 | | | | | | |
| TCC | TCT | CAA | GGG | GAG | ACT | AAT | ATT | AAG | CTA | ATA | TTT | ACT | GAA | AAG | AAA | 4774 |
| Ser | Ser | Gln | Gly | Glu | Thr | Asn | Ile | Lys | Leu | Ile | Phe | Thr | Glu | Lys | Lys | |
| 75 | | | | 80 | | | | | 85 | | | | | | 90 | |
| AGT | CTG | GCC | AGA | AAA | ACA | TTA | AAC | TTA | AAA | GGA | TAT | AAG | AGA | TTT | TTA | 4822 |
| Ser | Leu | Ala | Arg | Lys | Thr | Leu | Asn | Leu | Lys | Gly | Tyr | Lys | Arg | Phe | Leu | |
| | | | 95 | | | | | 100 | | | | | 105 | | | |
| TAT | GAA | TCA | GAT | AGA | TGC | ATT | CAT | TAT | GTC | GAT | AAA | ATG | AAT | CTC | AAT | 4870 |
| Tyr | Glu | Ser | Asp | Arg | Cys | Ile | His | Tyr | Val | Asp | Lys | Met | Asn | Leu | Asn | |
| | | 110 | | | | | 115 | | | | | 120 | | | | |
| TCT | CAT | ACT | GTT | AAA | TGT | GTA | GGT | TCA | TTC | ACA | AGA | GGA | GTA | GAT | TTC | 4918 |
| Ser | His | Thr | Val | Lys | Cys | Val | Gly | Ser | Phe | Thr | Arg | Gly | Val | Asp | Phe | |
| | | 125 | | | | | 130 | | | | | 135 | | | | |
| ACT | TTA | TAT | ATC | CCA | CAA | GGT | GAA | ATT | GAT | GGG | CTT | CTA | ACT | GGA | GGT | 4966 |
| Thr | Leu | Tyr | Ile | Pro | Gln | Gly | Glu | Ile | Asp | Gly | Leu | Leu | Thr | Gly | Gly | |
| 140 | | | | | 145 | | | | | 150 | | | | | | |
| ATA | TGG | GAG | GCA | ACA | CTA | GAG | TTA | CGA | GTC | AAA | AGG | CAT | TAC | GAC | TAT | 5014 |
| Ile | Trp | Glu | Ala | Thr | Leu | Glu | Leu | Arg | Val | Lys | Arg | His | Tyr | Asp | Tyr | |
| 155 | | | | 160 | | | | | 165 | | | | | 170 | | |
| AAT | CAT | GGT | ACT | TAC | AAA | GTT | AAT | ATC | ACA | GTT | GAT | TTG | ACA | GAC | AAA | 5062 |
| Asn | His | Gly | Thr | Tyr | Lys | Val | Asn | Ile | Thr | Val | Asp | Leu | Thr | Asp | Lys | |

-continued

```
                         175                 180                 185
GGA AAT ATT CAG GTC TGG ACA CCA AAG TTT CAT AGC GAT CCT AGA ATT      5110
Gly Asn Ile Gln Val Trp Thr Pro Lys Phe His Ser Asp Pro Arg Ile
            190                 195                 200

GAT CTG AAT TTA CGT CCT GAA GGT AAT GGT AAA TAT TCT GGT AGT AAC      5158
Asp Leu Asn Leu Arg Pro Glu Gly Asn Gly Lys Tyr Ser Gly Ser Asn
            205                 210                 215

GTG CTT GAG ATG TGT CTC TAT GAT GGC TAT AGT ACA CAT AGT CAA AGT      5206
Val Leu Glu Met Cys Leu Tyr Asp Gly Tyr Ser Thr His Ser Gln Ser
            220                 225                 230

ATA GAA ATG AGG TTT CAG GAT GAC TCA CAA ACA GGA AAT AAT GAA TAT      5254
Ile Glu Met Arg Phe Gln Asp Asp Ser Gln Thr Gly Asn Asn Glu Tyr
235                 240                 245                 250

AAT CTT ATA AAA ACT GGA GAG CCA TTA AAA AAA TTG CCA TAT AAA CTT      5302
Asn Leu Ile Lys Thr Gly Glu Pro Leu Lys Lys Leu Pro Tyr Lys Leu
                255                 260                 265

TCT CTT CTT TTA GGA GGA CGA GAG TTT TAT CCA AAT AAT GGA GAG GCT      5350
Ser Leu Leu Leu Gly Gly Arg Glu Phe Tyr Pro Asn Asn Gly Glu Ala
            270                 275                 280

TTT ACT ATT AAT GAT ACT TCG TCA TTG TTT ATA AAC TGG AAT CGT ATT      5398
Phe Thr Ile Asn Asp Thr Ser Ser Leu Phe Ile Asn Trp Asn Arg Ile
            285                 290                 295

AAG TCT GTA TCC TTA CCA CAG ATT AGT ATT CCA GTA CTA TGC TGG CCA      5446
Lys Ser Val Ser Leu Pro Gln Ile Ser Ile Pro Val Leu Cys Trp Pro
            300                 305                 310

GCA AAC TTG ACA TTT ATG TCA GAG CTA AAT AAT CCA GAA GCG GGT GAG      5494
Ala Asn Leu Thr Phe Met Ser Glu Leu Asn Asn Pro Glu Ala Gly Glu
315                 320                 325                 330

TAT TCA GGA ATA CTT AAC GTA ACA TTT ACT CCT AGT AGT TCA AGT CTG      5542
Tyr Ser Gly Ile Leu Asn Val Thr Phe Thr Pro Ser Ser Ser Ser Leu
                335                 340                 345

TAA AAATAGTATC TTTATAAATT ATGCTATTTG CGGGAGACTT TATCAGCTGG           5595
*

GAATTAGAGT CGCAATGATG TTTATCGGTA AACCAGCACC ATACTTCGGA AAATGCTGGC    5655

AAGCTTACGC CAATCTTTTT AGATTGAGTT GTTGGTATTA GATATCATAG TAAATGGTTA    5715

GCTTGTAAAG TTAGCGCTAT CATGAAATAT TTGATTTTTA TAATATTAAA AGAGTCCCTC    5775

TGAAGGTGGA CTGCACCCCA AAA                                            5798
```

(2) INFORMATION FOR SEQ ID NO:2:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ile Leu Leu Phe Val Ile Leu Phe Phe Asn Val Phe Ala Ala
-18             -15                 -10                 -5

Ser Ala Asn Phe Met Val Tyr Pro Ile Ser Lys Asp Ile Gln Ser Gly
            1               5                   10

Gly Ser Glu Thr Ile Lys Val Phe Ser Lys Ser Lys Asp Val Gln Tyr
15                  20                  25                  30

Ile Lys Ile Tyr Thr Lys Arg Val Ile Asn Pro Gly Thr Lys Glu Glu
                35                  40                  45

Gln Glu Val Asp Ile Lys Asn Trp Asp Gly Gly Leu Ile Val Thr Pro
            50                  55                  60
```

```
Ala Lys Val Val Leu Pro Ala Gly Ala Ser Lys Ser Ile Arg Leu Thr
        65                  70                  75

Glu Ile Asn Lys Lys Glu Gln Glu Val Tyr Arg Val Tyr Phe Glu
        80                  85                  90

Ser Val Lys Pro Gly Gln Gln Asp Asp Ile Glu Lys Asn Gly Arg
 95              100                 105                 110

Val Asn Thr Asp Leu Ser Val Asn Ile Ile Tyr Ala Ala Leu Ile Arg
                115                 120                 125

Thr Ser Pro Glu Asn Pro Gln Arg Lys Leu Asp Val Ser Ile Glu Ser
            130                 135                 140

Asn Asn Val Trp Ile Lys Asn Thr Gly Asn Ile Arg Leu Gly Ile Lys
            145                 150                 155

Asp Val Phe Leu Cys Asp Thr Ser Ile Asn Asp Lys Cys Ala Lys
        160                 165                 170

Phe Ser Tyr Asn Arg Asn Leu Tyr Pro Asp Met Ser Val Asp Thr Lys
175                 180                 185                 190

Leu Gly Lys Lys Gly Phe Ser Tyr Ala Val Ile Asp Thr Lys Asp Asp
                195                 200                 205

Arg Asn Glu Asn Ser Gly Glu Leu Ile Asn Ile Lys Leu Pro
            210                 215                 220

(2) INFORMATION FOR SEQ ID NO:3:

(i) SEQUENCE CHARACTERISTICS:
        (A) LENGTH:  170 amino acids
        (B) TYPE: amino acid
        (D) TOPOLOGY: linear (ii) MOLECULE TYPE: protein (xi) SEQUENCE DESCRIPTION: SEQ ID NO:3:

Met Lys Leu Asn Lys Ile Ile Gly Ala Leu Val Leu Ser Ser Thr Phe
-23             -20                 -15                 -10

Val Ser Met Gly Ala Ser Ala Ala Glu Lys Asn Ile Thr Val Thr Ala
         -5                   1                   5

Ser Val Asp Pro Thr Ile Asp Leu Met Gln Ser Asp Gly Thr Ala Leu
 10                  15                  20                  25

Pro Ser Ala Val Asn Ile Ala Tyr Leu Pro Gly Glu Lys Arg Phe Glu
                 30                  35                  40

Ser Ala Arg Ile Asn Thr Gln Val His Thr Asn Asn Lys Thr Lys Gly
                 45                  50                  55

Ile Gln Ile Lys Leu Thr Asn Asp Asn Val Val Met Thr Asn Leu Ser
         60                  65                  70

Asp Pro Ser Lys Thr Ile Pro Leu Glu Val Ser Phe Ala Gly Thr Lys
         75                  80                  85

Leu Ser Thr Ala Ala Thr Ser Ile Thr Ala Asp Gln Leu Asn Phe Gly
 90                  95                 100                 105

Ala Ala Gly Val Glu Thr Val Ser Ala Thr Lys Glu Leu Val Ile Asn
                110                 115                 120

Ala Gly Ser Thr Gln Gln Thr Asn Ile Val Ala Gly Asn Tyr Gln Gly
                125                 130                 135

Leu Val Ser Ile Val Leu Thr Gln Glu Pro
                140                 145

(2) INFORMATION FOR SEQ ID NO:4:

(i) SEQUENCE CHARACTERISTICS:
        (A) LENGTH:  866 amino acids
```

(B) TYPE: amino acid
(D) TOPOLOGY: linear (ii) MOLECULE TYPE: protein (xi) SEQUENCE DESCRIPTION: SEQ ID NO:4:

```
Met Arg Ala Phe Asn Lys Ile Thr Val Phe Ile Leu Phe Ile Pro Gly
-26 -25              -20              -15

Leu Cys Phe Gly Thr Asn Gly Leu Glu Ser Lys Lys Asn Ile Pro Glu
-10              -5                1                5

Glu Phe Ile Asp Leu Trp Met Glu Gln Asp Glu Leu Leu Glu Val Asn
                 10              15              20

Leu Tyr Gly Arg Ser Leu Gly Val His Arg Val Leu Thr Thr Pro Thr
             25              30              35

Thr Val Lys Phe Ser Ser Val Glu Glu Ile Leu Glu Lys Ile Asn Val
         40              45              50

Lys Gln Glu Lys Lys Glu Asp Leu Arg Ser Leu Leu Gln Ser Tyr
 55              60              65              70

Ser Arg Asn Gly Asn Met Ser Cys Asn Gly Phe Asp Glu Lys Glu Tyr
             75              80              85

Ser Cys Asn Tyr Ile Arg Thr Asp Thr Val Asn Val Ile Val Asp Glu
             90              95              100

Glu Asn Asn Glu Leu Asn Leu Phe Ile Gly Ala Ser Phe Leu Ser Val
     105             110             115

Gln Ala Gln Asp Asn Ile Tyr Tyr Gln Lys Asn Ile Asn Ser Glu Lys
 120             125             130

Ala Phe Ile His Ser Gln Thr Ile Asn Phe Ser Glu Ser Glu Gly Tyr
 135             140             145             150

Lys Ser Leu Ser Leu Lys Gly Val Gly Ala Gln Gly Leu Thr Glu Asn
             155             160             165

Ser Tyr Leu Val Phe Gly Trp Asp Ala Ile Tyr Asn Ser Ser Arg Lys
             170             175             180

Tyr Thr Tyr Lys Asn Gln Ser Ile Asn Asn Ile Tyr Tyr Arg Tyr Asp
         185             190             195

Phe Asp Lys Lys Tyr Tyr Tyr Gln Leu Gly Arg Met Asp Arg Ser Asp
 200             205             210

Leu Ser Ser Ala Ser Ser Gly Asn Phe Asn Phe Asn Met Leu Pro Leu
215             220             225             230

Pro Asp Ile Asp Gly Phe Gln Ile Gly Thr Thr Gln Ser Tyr Ile Lys
             235             240             245

Asn Ile Glu Lys Ser Ile Ser Ser Pro Val Thr Val Met Leu Thr Arg
         250             255             260

Phe Ser Arg Val Glu Ala Phe Arg Asn Glu Glu Leu Leu Gly Val Trp
         265             270             275

Tyr Leu Asn Ser Gly Ile Asn Asp Leu Asp Thr Ser Arg Leu Pro Asp
 280             285             290

Gly Ser Tyr Asp Leu Thr Leu Lys Ile Phe Glu Gln Asp Ile Leu Val
295             300             305             310

Arg Glu Glu Lys Val Pro Phe Asn Lys Gly Ala Ser Phe Gly Asp
             315             320             325

Met Gln Trp Asp Val Phe Ala Gln Ala Gly Asn Ile Val Asn Asn Asn
             330             335             340

Asp Ser Tyr Ile Glu Lys Gln Thr Asn Lys Lys Thr Gly Ile Asn Ala
             345             350             355

Gly Ile Arg Thr Pro Val Thr Arg Asn Leu Ser Phe Leu Gln Gly Gly
```

```
              360                 365                 370
Ala Ile Ile Asp Asn Asp Lys Tyr Tyr Glu Ala Gly Val Asn Trp Arg
375                 380                 385                 390

Ser Gly Phe Leu Asp Gly Val Leu Ser Gly Asn Phe Ser Phe Leu Tyr
                395                 400                 405

Gly Asp Gly Ala Arg Gly Asn Tyr Gln Asn Ile Ser Tyr Thr Asp Gly
                410                 415                 420

Phe Asn Leu Ser Phe Tyr Arg Asn Asp Lys Ser Val Asp Asn Cys Ser
                425                 430                 435

His Asn Tyr Ser Ala Gly Trp Ser Gly Cys Tyr Glu Ser Tyr Ser Phe
440                 445                 450

Ser Leu Ser Val Pro Val Ser Gly Trp Thr Thr Thr Leu Gly Tyr Asn
455                 460                 465                 470

His Thr Asn Asn Glu Ala Val His Lys Tyr Asp Tyr Thr Pro Glu Tyr
                475                 480                 485

Phe Phe Ser Lys Lys Tyr Lys Gly Val Ser Lys Arg Trp Gln Leu Thr
                490                 495                 500

Ser Ser Ser Ser Tyr Lys Trp Met Asp Tyr His Val Ile Pro Thr Ile
                505                 510                 515

Gly Val Tyr Arg Ser Asp Gln Ser Arg Trp Ser Glu Gln Gly Gly Tyr
520                 525                 530

Phe Ser Leu Ser Phe Thr Arg Val Lys Glu Asn Ser Ala Ile Asn Ala
535                 540                 545                 550

Gly Tyr Ser Tyr Asn Tyr Val Lys His Lys Asn Ala Thr His Glu Ala
                555                 560                 565

Phe Leu Asp Gly Arg Ile Thr Thr Asn Thr Phe Gly Tyr Ser Glu Leu
                570                 575                 580

Gly Ser Arg Ile Asn Thr Asn Lys Asn Asn Thr Glu Ala Gly Val Thr
                585                 590                 595

Gly Arg Val Lys Asn Arg Phe Gly Asp Leu Asn Gly Ser Leu Asn Val
                600                 605                 610

Asn Lys Ser Lys Thr Ser Gly Lys Met Thr His Ser Met Ser Ala Asn
615                 620                 625                 630

Tyr Asn Ser Ser Phe Ala Ile Thr Gly Asp Ser Val Tyr Trp Gly Gly
                635                 640                 645

Asp Ala Ser Gly Leu Thr Lys Leu Ser Gly Gly Val Val Asn Val Arg
                650                 655                 660

Ser Asp Lys Ser Lys Glu Leu Ile Lys Ile Ser Gly Ser Ser Tyr
                665                 670                 675

Gly Asn Tyr Ile Leu Gly Ser Asn Asp Arg Ser Phe Ile Pro Val Ser
                680                 685                 690

Ala Leu Met Pro Ser Asn Leu Thr Ile Glu Glu Ile Gln Ser Asn Asp
695                 700                 705                 710

Lys Asn Ile Thr Val Gln Ala Leu Ser Lys Asn Asp Phe Phe Ile Leu
                715                 720                 725

Pro Gly Asn Val Phe Pro Ile Asp Val Thr Ala Asn Val Thr Val Ser
                730                 735                 740

Tyr Ile Gly Arg Ala Leu Asp Asp Lys Gly Asn Pro Leu Ser Asn Ala
                745                 750                 755

His Ile Leu Asp Val His Gly Val Arg Leu Asp Glu Asp Gly Gly Phe
                760                 765                 770

Ser Phe Glu Thr Ser Ala Gln Lys Lys Ser Leu Phe Leu Leu Lys Asp
775                 780                 785                 790
```

```
Lys Asp Ile Tyr Ser Cys Asp Val Lys Lys Tyr Asp Leu Arg Ser Gly
            795                 800                 805

Val Leu Phe Thr Gly Asp Leu Ile Cys Glu His Ser Gly Ile Glu Arg
            810                 815                 820

Leu Gly Lys Asp Leu Val Asn Asn Pro Arg Val Lys Gln Leu Leu Ala
            825                 830                 835

Tyr Lys
    840
```

(2) INFORMATION FOR SEQ ID NO:5:

(i) SEQUENCE CHARACTERISTICS:
        (A) LENGTH: 364 amino acids
        (B) TYPE: amino acid
        (D) TOPOLOGY: linear (ii) MOLECULE TYPE: protein (xi) SEQUENCE DESCRIPTION: SEQ ID NO:5:

```
Leu Lys Lys Val Ile Phe Val Leu Ser Met Phe Leu Cys Ser Gln Val
-18         -15             -10                 -5

Tyr Gly Gln Ser Trp His Thr Asn Val Glu Ala Gly Ser Ile Asn Lys
    1                5                   10

Thr Glu Ser Ile Gly Pro Ile Asp Arg Ser Ala Ala Ser Tyr Pro
 15              20                  25                  30

Ala His Tyr Ile Phe His Glu His Val Ala Gly Tyr Asn Lys Asp His
                 35                  40                  45

Ser Leu Phe Asp Arg Met Thr Phe Leu Cys Met Ser Ser Thr Asp Ala
             50                  55                  60

Ser Lys Gly Ala Cys Pro Thr Gly Glu Asn Ser Lys Ser Ser Gln Gly
         65                  70                  75

Glu Thr Asn Ile Lys Leu Ile Phe Thr Glu Lys Lys Ser Leu Ala Arg
     80                  85                  90

Lys Thr Leu Asn Leu Lys Gly Tyr Lys Arg Phe Leu Tyr Glu Ser Asp
 95             100                 105                 110

Arg Cys Ile His Tyr Val Asp Lys Met Asn Leu Asn Ser His Thr Val
                115                 120                 125

Lys Cys Val Gly Ser Phe Thr Arg Gly Val Asp Phe Thr Leu Tyr Ile
            130                 135                 140

Pro Gln Gly Glu Ile Asp Gly Leu Leu Thr Gly Gly Ile Trp Glu Ala
            145                 150                 155

Thr Leu Glu Leu Arg Val Lys Arg His Tyr Asp Tyr Asn His Gly Thr
    160                 165                 170

Tyr Lys Val Asn Ile Thr Val Asp Leu Thr Asp Lys Gly Asn Ile Gln
175                 180                 185                 190

Val Trp Thr Pro Lys Phe His Ser Asp Pro Arg Ile Asp Leu Asn Leu
                195                 200                 205

Arg Pro Glu Gly Asn Gly Lys Tyr Ser Gly Ser Asn Val Leu Glu Met
            210                 215                 220

Cys Leu Tyr Asp Gly Tyr Ser Thr His Ser Gln Ser Ile Glu Met Arg
            225                 230                 235

Phe Gln Asp Asp Ser Gln Thr Gly Asn Asn Glu Tyr Asn Leu Ile Lys
        240                 245                 250

Thr Gly Glu Pro Leu Lys Lys Leu Pro Tyr Lys Leu Ser Leu Leu Leu
255                 260                 265                 270

Gly Gly Arg Glu Phe Tyr Pro Asn Asn Gly Glu Ala Phe Thr Ile Asn
            275                 280                 285
```

```
Asp Thr Ser Ser Leu Phe Ile Asn Trp Asn Arg Ile Lys Ser Val Ser
            290                 295                 300

Leu Pro Gln Ile Ser Ile Pro Val Leu Cys Trp Pro Ala Asn Leu Thr
            305                 310                 315

Phe Met Ser Glu Leu Asn Asn Pro Glu Ala Gly Glu Tyr Ser Gly Ile
            320                 325                 330

Leu Asn Val Thr Phe Thr Pro Ser Ser Ser Ser Leu
335                 340                 345
```

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (xi) SEQUENCE DESCRIPTION: SEQ ID NO:6:

CGCTGGGTGC CGTGAGCAC                                          19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (xi) SEQUENCE DESCRIPTION: SEQ ID NO:7:

TCGGCAGCGC AGAGCCATC                                          19

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (xi) SEQUENCE DESCRIPTION: SEQ ID NO:8:

AAGACCTCGA GTGTAAAACG ACGGCCAG                            28

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "Oligonucleotide primer for PCR."

(iii) HYPOTHETICAL: NO (xi) SEQUENCE DESCRIPTION: SEQ ID NO:9:

TAGTAGTCTC GAGCGGCCGC CAAGCTTGCA TGCCT                              35

(2) INFORMATION FOR SEQ ID NO:10:

(i) SEQUENCE CHARACTERISTICS:
     (A) LENGTH: 171 amino acids
     (B) TYPE: amino acid
     (C) STRANDEDNESS:
     (D) TOPOLOGY: unknown (ii) MOLECULE TYPE: protein (iii) HYPOTHETICAL: NO (xi) SEQUENCE DESCRIPTION: SEQ ID NO:10:

Met Lys Leu Lys Lys Thr Ile Gly Ala Met Ala Leu Ala Thr Leu Phe
1               5                   10                  15

Ala Thr Met Gly Ala Ser Ala Val Glu Lys Thr Ile Ser Val Thr Ala
            20                  25                  30

Ser Val Asp Pro Thr Val Asp Leu Leu Gln Ser Asp Gly Ser Ala Leu
        35                  40                  45

Pro Asn Ser Val Ala Leu Thr Tyr Ser Pro Ala Val Asn Asn Phe Glu
    50                  55                  60

Ala His Thr Ile Asn Thr Val His Thr Asn Asp Ser Asp Lys Gly
65              70                  75                  80

Val Val Val Lys Leu Ser Ala Asp Pro Val Leu Ser Asn Val Leu Asn
                85                  90                  95

Pro Thr Leu Gln Ile Pro Val Ser Val Asn Phe Ala Gly Lys Pro Leu
            100                 105                 110

Ser Thr Thr Gly Ile Thr Ile Asp Ser Asn Asp Leu Asn Phe Ala Ser
        115                 120                 125

Ser Gly Val Asn Lys Val Ser Ser Thr Gln Lys Leu Ser Ile His Ala
    130                 135                 140

Asp Ala Thr Arg Val Thr Gly Gly Ala Leu Thr Ala Gly Gln Tyr Gln
145                 150                 155                 160

Gly Leu Val Ser Ile Ile Leu Thr Lys Ser Thr
                165                 170

(2) INFORMATION FOR SEQ ID NO:11:

(i) SEQUENCE CHARACTERISTICS:
     (A) LENGTH: 170 amino acids
     (B) TYPE: amino acid
     (C) STRANDEDNESS:
     (D) TOPOLOGY: unknown (ii) MOLECULE TYPE: protein (iii) HYPOTHETICAL: NO (xi) SEQUENCE DESCRIPTION: SEQ ID NO:11:

Met Lys Phe Lys Lys Thr Ile Gly Ala Met Ala Leu Thr Thr Met Phe
1               5                   10                  15

Val Ala Val Ser Ala Ser Ala Val Glu Lys Asn Ile Thr Val Thr Ala
            20                  25                  30

Ser Val Asp Pro Ala Ile Asp Leu Leu Gln Ala Asp Gly Asn Ala Leu
        35                  40                  45

```
Pro Ser Ala Val Lys Leu Ala Tyr Ser Pro Ala Ser Lys Thr Phe Glu
    50                  55                  60

Ser Tyr Arg Val Met Thr Gln Val His Thr Asn Asp Ala Thr Lys Lys
65                  70                  75                  80

Val Ile Val Lys Leu Ala Asp Thr Pro Gln Leu Thr Asp Val Leu Asn
                85                  90                  95

Ser Thr Val Gln Met Pro Ile Ser Val Ser Trp Gly Gly Gln Val Leu
                100                 105                 110

Ser Thr Thr Ala Lys Glu Phe Glu Ala Ala Leu Gly Tyr Ser Ala
                115                 120                 125

Ser Gly Val Asn Gly Val Ser Ser Ser Gln Glu Leu Val Ile Ser Ala
    130                 135                 140

Ala Pro Lys Thr Ala Gly Thr Ala Pro Thr Ala Gly Asn Tyr Ser Gly
145                 150                 155                 160

Val Val Ser Leu Val Met Thr Leu Gly Ser
                165                 170
```

(2) INFORMATION FOR SEQ ID NO:12:

(i) SEQUENCE CHARACTERISTICS:
      (A) LENGTH: 238 amino acids
      (B) TYPE: amino acid
      (C) STRANDEDNESS:
      (D) TOPOLOGY: unknown (ii) MOLECULE TYPE: protein (iii) HYPOTHETICAL: NO (xi) SEQUENCE DESCRIPTION: SEQ ID NO:12:

```
Met Arg Lys Leu Phe Leu Ser Leu Leu Met Ile Pro Phe Val Ala Lys
1               5                   10                  15

Ala Asn Phe Met Ile Tyr Pro Ile Ser Lys Glu Ile Lys Gly Gly Ser
                20                  25                  30

Ser Glu Leu Ile Arg Ile Tyr Ser Lys Ser Lys Asp Thr Gln Tyr Ile
                35                  40                  45

Lys Val Tyr Thr Lys Lys Val Leu Asn Pro Gly Thr Lys Glu Glu Tyr
    50                  55                  60

Glu Val Asp Thr Pro Asn Trp Glu Gly Gly Leu Val Thr Thr Pro Ser
65                  70                  75                  80

Lys Val Ile Leu Pro Gly Gly Gly Ser Lys Ser Val Arg Leu Ser Gln
                85                  90                  95

Leu Lys Asp Ile Ser Ser Glu Asp Val Tyr Arg Val Tyr Phe Glu Ser
                100                 105                 110

Ile Lys Pro Glu Lys Gln Asp Gly Leu Ser Lys Asn Lys Ser Leu Lys
                115                 120                 125

Thr Asp Leu Ser Val Asn Ile Ile Tyr Ala Ala Leu Ile Arg Val Leu
                130                 135                 140

Pro Lys Asp Gly Lys Ser Asp Met Arg Ala Ser Leu Ser Pro Lys Ser
145                 150                 155                 160

Ser Leu Leu Ile Lys Asn Thr Gly Asn Val Arg Val Gly Ile Lys Asp
                165                 170                 175

Ala Phe Phe Cys Lys Lys Thr Ser Ile Asn Asn Asp Cys Ile Lys
                180                 185                 190

Lys Thr Tyr Asn Lys Asn Ile Tyr Pro Gly Ser Ser Phe Asp Thr Gly
                195                 200                 205

Val Ile Gln Asn Gly Phe Ser His Ile Phe Ile Asp Ser Val Asp Gly
```

```
                  210                 215                 220
        Ser Ala Gly Lys Gln Gly Lys Arg Met Leu Ile Ser Ile His
        225                 230                 235

(2) INFORMATION FOR SEQ ID NO:13:

(i) SEQUENCE CHARACTERISTICS:
        (A) LENGTH: 238 amino acids
        (B) TYPE: amino acid
        (C) STRANDEDNESS:
        (D) TOPOLOGY: unknown (ii) MOLECULE TYPE: protein (iii) HYPOTHETICAL: NO (xi) SEQUENCE DESCRIPTION: SEQ ID NO:13:

Met His Lys Leu Phe Tyr Leu Ser Leu Leu Met Ala Pro Phe Val
        1               5                   10                  15

Ala Asn Ala Asn Phe Met Ile Tyr Pro Ile Ser Lys Asp Leu Lys Asn
                    20                  25                  30

Gly Asn Ser Glu Leu Val Arg Val Tyr Ser Lys Ser Lys Glu Ile Gln
                    35                  40                  45

Tyr Ile Lys Ile Tyr Thr Lys Lys Ile Ile Asn Pro Gly Thr Thr Glu
        50                  55                  60

Glu Tyr Lys Val Asp Ile Pro Asn Trp Asp Gly Gly Leu Val Val Thr
        65                  70                  75                  80

Pro Gln Lys Val Ile Leu Pro Ala Gly Ala Ser Lys Ser Ile Arg Leu
                        85                  90                  95

Thr Gln Phe Lys Ile Pro Lys Lys Glu Glu Val Tyr Arg Val Tyr Phe
                        100                 105                 110

Glu Ala Val Lys Pro Asp Ser Lys Glu Asn Val Ile Asp Asn Lys Lys
                        115                 120                 125

Leu Thr Thr Glu Leu Ser Val Asn Ile Ile Tyr Ala Ala Leu Ile Arg
        130                 135                 140

Ser Leu Pro Ser Glu Gln Asn Ile Ser Leu Asn Ile Ser Arg Asn Ala
        145                 150                 155                 160

Lys Lys Asn Ile Ile Ile Tyr Asn Asn Gly Asn Val Arg Ala Gly Val
                        165                 170                 175

Lys Asp Ile Tyr Phe Cys Lys Ser Ser Asn Ile Asp Asp Asn Cys Val
                        180                 185                 190

Lys Lys Ala Tyr Asn Lys Asn Ile Tyr Pro Glu Lys Ser Phe Asp Thr
                        195                 200                 205

Leu Val Asn Asn Asn Phe Ser Tyr Val Phe Ile Lys Leu Asn His Glu
                        210                 215                 220

Gly Ile Glu Lys Glu Gln Gly Leu Ile Gln Leu Lys Val Pro
        225                 230                 235

(2) INFORMATION FOR SEQ ID NO:14:

(i) SEQUENCE CHARACTERISTICS:
        (A) LENGTH: 890 amino acids
        (B) TYPE: amino acid
        (C) STRANDEDNESS:
        (D) TOPOLOGY: unknown (ii) MOLECULE TYPE: protein (iii) HYPOTHETICAL: NO (xi) SEQUENCE DESCRIPTION: SEQ ID NO:14:
```

```
Cys Cys Met Ile Gly Gly Lys Ser Ser Lys Val Val Ile Val Leu Ser
1               5                   10                  15

Val Leu Ile Gly Ser Ser Ser Gly Phe Ala Ser Lys Tyr Asn Leu Val
            20                  25                  30

Asp Ile Pro Glu Ser Phe Arg Asp Leu Trp Gly Gln Asp Glu Leu
        35                  40                  45

Leu Glu Val Arg Cys Cys Leu Tyr Gly Gln Ser Leu Gly Val His Arg
    50                  55                  60

Ile Lys Ser Thr Pro Thr Thr Val Ala Phe Glu Ser Pro Asp Asn Leu
65              70                  75                      80

Leu Asp Lys Ile Glu Ile Asn Lys Gly Lys Glu Ala Asp Leu Arg Val
                85              90                  95

Leu Met Arg Gly Ser Phe Gln Arg Cys Cys Asn Gly Asn Met Ser Cys
            100                 105                 110

Gln Gly Tyr Thr Gly Gln Asn Asn Cys Asn Tyr Ile Lys Thr Asn Thr
            115                 120                 125

Val Ala Val Ile Val Asp Asp Val Glu Asn Val Leu Asn Leu Phe Ile
    130                 135                 140

Gly Asn Glu Phe Leu Ala Ser Gly Glu Asn Asp Cys Cys Ser Asp Tyr
145             150                 155                 160

Tyr Gln Pro Ser Lys Asn Thr Lys Lys Ala Phe Ile His Ser Gln Thr
                165                 170                 175

Ile Asn Leu Ser Asp Thr Gly Asn Tyr Glu Asn Leu Ser Ile Val Gly
            180                 185                 190

Thr Gly Ser Leu Gly Ile Thr Asp Asn Ser Tyr Ala Ile Leu Gly Cys
        195                 200                 205

Cys Trp Ala Ala Asn Tyr Asn Arg Tyr Lys Ser Tyr Asn Tyr Asn Glu
    210                 215                 220

Gln Ser Ile Asn Ser Leu Tyr Phe Arg His Asp Phe Glu Lys Asn Phe
225             230                 235                     240

Tyr Tyr Gln Leu Gly Arg Ile Asp Arg Ser Asp Leu Ser Gln Ser Ser
                245                 250                 255

Gly Gly Asn Cys Cys Phe Asn Phe Asp Leu Leu Pro Val Pro Asp Ile
            260                 265                 270

Tyr Gly Met Arg Ala Gly Thr Thr Gln Ser Tyr Ile Lys Asn Thr Gly
        275                 280                 285

Lys Ser Val Ala Ser Pro Val Thr Ile Met Leu Thr His Phe Ser Arg
290                 295                 300

Val Glu Ala Tyr Arg Asn Gly Cys Cys Gln Leu Leu Gly Val Trp Tyr
305                 310                 315                 320

Leu Asp Ala Gly Ile Ser Glu Leu Asp Thr Glu Arg Leu Pro Asp Gly
            325                 330                 335

Asn Tyr Asp Leu Lys Leu Lys Ile Phe Glu Gln Glu Gln Leu Val Arg
            340                 345                 350

Glu Glu Ile Val Pro Phe Asn Lys Ser Gly Ser Cys Cys Ser Ile Gly
            355                 360                 365

Asp Thr His Trp Asp Val Phe Val Gln Ala Gly Asp Ile Ile Asn Asp
        370                 375                 380

Asn Gly Arg Tyr Val Glu Lys Gln Lys Asn His Lys Ser Ala Ile Asn
385                 390                 395                 400

Ser Gly Leu Arg Leu Pro Leu Thr Arg Asn Leu Ala Val Gln Leu Cys
            405                 410                 415

Cys Gly Gly Ala Val Ile Asp Asn Lys Asn Tyr Tyr Glu Thr Gly Ile
            420                 425                 430
```

-continued

```
Leu Trp Asn Ser Gly Leu Leu Asp Gly Ser Leu Asn Ser Lys Phe Thr
        435                 440                 445
Phe Leu Phe Gly Asp Asp Thr His Gly Asn Tyr Gln Asn Val Ser Tyr
450                 455                 460
Thr Asp Gly Phe Ser Leu Ser Phe Tyr His Asn Asp Lys Arg Val Asp
465                 470                 475                 480
Asp Cys Gly Lys Asp Tyr Asn Met Gly Trp Ser Gly Cys Tyr Glu Ser
                485                 490                 495
Tyr Ser Ala Ser Leu Ser Ile Pro Val Lys Gly Trp Asn Ser Thr Leu
                500                 505                 510
Ala Tyr Ser Asn Thr Tyr Ser Thr Ser Val Tyr Arg Tyr Asp Ala Val
                515                 520                 525
Ser Glu Tyr Val Pro Tyr Tyr Tyr Lys Gly Arg Thr Lys Arg Trp
530                 535                 540
Gln Leu Thr Ala Ser Thr Val Val Arg Trp Gly Asp Tyr Asn Ile Met
545                 550                 555                 560
Pro Thr Ile Gly Val Tyr Asn Ser Glu Gln Lys Gln Trp Ala Asp Lys
                565                 570                 575
Gly Gly Tyr Leu Ser Leu Thr Leu Thr Arg Val Asp Gly Gly Lys Ser
                580                 585                 590
Leu Asn Ala Gly Tyr Ser Tyr Asn Tyr Ser Arg Gly Asn Tyr Thr Ser
                595                 600                 605
Asn Asp Ala Phe Val Glu Gly His Leu Val Ser Asp Thr Asn Val Ser
610                 615                 620
Tyr Arg Glu Leu Ser Ala Arg Val Ser Gly Asn Arg Tyr Tyr Thr Glu
625                 630                 635                 640
Gly Gly Val Ser Gly Arg Ile Asn Asn Arg Phe Gly Asp Leu Asn Gly
                645                 650                 655
Thr Leu Asn Val Asn Lys Asn Arg Lys Ser His Asp Thr Thr His Ser
                660                 665                 670
Leu Thr Ala Gly Tyr Ser Ser Ser Phe Ala Leu Thr Thr Asp Gly Ile
                675                 680                 685
Tyr Trp Gly Gly Ser Ala Ser Gly Leu Thr Asn Leu Ser Gly Gly Ile
690                 695                 700
Val Arg Val Lys Ser Asn Glu Asp Glu Ser Glu Leu Leu Asn Val Lys
705                 710                 715                 720
Gly Ser Ser Tyr Gly His Tyr Ser Leu Gly Ser Asn Asp Ser Leu Phe
                725                 730                 735
Ile Pro Val Pro Ala Leu Met Gln Ala Ser Leu Thr Ile Glu Glu Asn
                740                 745                 750
Thr Asn Lys Ser Lys Asn Ile Asp Val Leu Ala Pro Thr Lys Asn Thr
                755                 760                 765
Phe Phe Met Leu Pro Gly Ser Val Tyr Pro Ile Asp Val Ser Ala Asn
770                 775                 780
Val Ser Phe Thr Tyr Val Gly Arg Gly Val Asp Val Lys Gly Arg Pro
785                 790                 795                 800
Leu Ser Gly Ala Tyr Ile Leu Asn Ala Gln Asn Ile Val Leu Asp Glu
                805                 810                 815
Asn Gly Gly Phe Ser Phe Glu Ser Ser Glu Asn Glu Lys Glu Leu Phe
                820                 825                 830
Leu Leu Lys Asp Lys Thr Ile Tyr Ser Cys Ser Leu Asp Arg Ser Glu
                835                 840                 845
Met Arg Asn Gly Ile Ala Phe Val Gly Glu Val Ala Cys Asn Ser Thr
```

-continued

```
                850                 855                 860

Ile Lys Glu Leu Leu Pro Glu Lys Leu Val Thr Asn Ser Arg Ile His
    865                 870                 875                 880

Asp Leu Leu Ala Tyr Asn Gln Asp Thr Glu
                    885                 890
```

(2) INFORMATION FOR SEQ ID NO:15:

(i) SEQUENCE CHARACTERISTICS:
        (A) LENGTH: 869 amino acids
        (B) TYPE: amino acid
        (C) STRANDEDNESS:
        (D) TOPOLOGY: unknown (ii) MOLECULE TYPE: protein (iii) HYPOTHETICAL: NO (xi) SEQUENCE DESCRIPTION: SEQ ID NO:15:

```
    Met Lys His Lys Lys Asn Arg Leu Val Ala Ile Ser Val Ala
    1               5                   10                  15

Leu Ile Pro Tyr Ile Gly Val Thr Gly Asp Ile Pro Asp Ser Phe Arg
                    20                  25                  30

Asp Leu Trp Gly Glu Gln Asp Glu Phe Tyr Glu Val Lys Leu Tyr Gly
                    35                  40                  45

Gln Thr Leu Gly Ile His Arg Ile Lys Thr Thr Pro Thr His Ile Lys
    50                  55                  60

Phe Tyr Ser Pro Glu Ser Ile Leu Asp Lys Ile Asn Leu Lys Lys Glu
    65                  70                  75                  80

Lys Glu Lys Glu Leu Ser Val Phe Phe Thr Asn Ser Phe Ser Arg Asn
                    85                  90                  95

Gly Asn Met Ser Cys Gln Gly Asn Thr Thr Ile Gln Tyr Asn Cys Asn
                    100                 105                 110

Tyr Ile Lys Thr Lys Ser Val Asp Val Ile Val Asp Val Asp Asn
                    115                 120                 125

Val Val Asn Leu Phe Ile Gly Asn Glu Phe Leu Asp Ser Glu Ala His
                    130                 135                 140

Asn Asp Glu Tyr His Gln Leu Ser Arg Asn Val Lys Lys Ala Phe Ile
    145                 150                 155                 160

Gln Ser Gln Thr Ile Asn Leu Ser Asp Ser Gly Lys Tyr Lys Arg Leu
                    165                 170                 175

Ser Ile Ser Gly Asn Ser Ala Leu Gly Ile Thr Asp Thr Ser Tyr Ala
                    180                 185                 190

Val Leu Asn Trp Trp Met Asn Tyr Asn Lys Ser Asn Gly Tyr Ser Asn
                    195                 200                 205

Asn Glu Lys Thr Ile Asn Ser Leu Tyr Phe Arg His Asp Leu Asp Lys
    210                 215                 220

Arg Tyr Tyr Tyr Gln Phe Gly Arg Met Asp Arg Thr Asp Leu Ser Gln
    225                 230                 235                 240

Ser Ile Ser Gly Ser Phe Asn Phe Asn Leu Leu Pro Leu Pro Asp Ile
                    245                 250                 255

Asp Gly Ile Arg Thr Gly Thr Thr Gln Ser Tyr Ile Lys Asn Thr Asp
                    260                 265                 270

Lys Phe Ile Ala Ser Pro Val Thr Val Met Leu Thr Asn Phe Ser Arg
                    275                 280                 285

Val Glu Ala Phe Arg Asn Asp Gln Leu Leu Gly Val Trp Tyr Leu Asp
                    290                 295                 300
```

```
Ser Gly Val Asn Glu Leu Asp Thr Ala Arg Leu Pro Tyr Gly Ser Tyr
305                 310                 315                 320

Asp Leu Lys Leu Lys Ile Phe Glu Asn Thr Gln Leu Val Arg Glu Glu
            325                 330                 335

Ile Ile Pro Phe Asn Lys Gly Arg Ser Ile Gly Asp Met Gln Trp
                340                 345                 350

Asp Ile Phe Val Gln Gly Gly Asn Ile Val Asn Asp Asn Asp Arg Tyr
        355                 360                 365

Ile Glu Lys Gln Asn Asn His Lys Ser Ser Ile Asn Thr Gly Leu Arg
    370                 375                 380

Leu Pro Ile Thr Lys Asn Ile Ser Val Gln Gln Gly Val Ser Val Ile
385                 390                 395                 400

Asp Asn Lys Ser Tyr Tyr Glu Gly Ser Leu Lys Trp Asn Ser Gly Ile
                405                 410                 415

Leu Ser Gly Ser Leu Asn Ser Glu Phe Ser Phe Leu Trp Gly Asp Asn
                420                 425                 430

Ala Lys Gly Asn Tyr Gln Ser Ile Ser Tyr Thr Asp Gly Phe Ser Leu
        435                 440                 445

Ser Phe Tyr His Asn Asp Lys Arg Val Asp Asn Cys Gly Arg Asn Tyr
    450                 455                 460

Asn Ala Gly Trp Ser Gly Cys Tyr Glu Ser Tyr Ser Ala Ser Leu Ser
465                 470                 475                 480

Ile Pro Leu Leu Gly Trp Thr Ser Thr Leu Gly Tyr Ser Asp Thr Tyr
                485                 490                 495

Ser Glu Ser Val Tyr Lys Ser His Ile Leu Ser Glu Tyr Gly Phe Tyr
                500                 505                 510

Asn Gln Asn Ile Tyr Lys Gly Arg Thr Gln Arg Trp Gln Leu Thr Ser
    515                 520                 525

Ser Thr Ser Leu Lys Trp Met Asp Tyr Asn Phe Met Pro Ala Ile Gly
530                 535                 540

Ile Tyr Asn Ser Glu Gln Arg Gln Leu Thr Asp Lys Gly Gly Tyr Ile
545                 550                 555                 560

Ser Val Thr Ile Thr Arg Ala Ser Arg Glu Asn Ser Leu Asn Thr Gly
                565                 570                 575

Tyr Ser Tyr Asn Tyr Ser Arg Gly Asn Tyr Ser Ser Asn Glu Leu Phe
                580                 585                 590

Val Asp Gly Tyr Met Thr Ser Thr Asn Asn Gly Asp Tyr His Glu Ala
        595                 600                 605

Gly Met Arg Phe Asn Lys Asn Arg His Asn Ala Glu Gly Arg Leu Ser
        610                 615                 620

Gly Arg Ile Asn Asn Arg Phe Gly Asp Leu Asn Gly Ser Phe Ser Met
625                 630                 635                 640

Asn Lys Asn Arg Asn Thr Asn Ser Thr Asn His Ser Leu Thr Gly Gly
                645                 650                 655

Tyr Asn Ser Ser Phe Ala Leu Thr Ser Asp Gly Phe Tyr Trp Gly Gly
        660                 665                 670

Ser Thr Ala Gly Leu Thr Lys Leu Ala Gly Gly Ile Ile Lys Val Lys
        675                 680                 685

Ser Asn Asp Thr Lys Lys Asn Leu Val Lys Val Thr Gly Thr Leu Tyr
        690                 695                 700

Gly Asp Tyr Ser Leu Gly Ser Asn Asp Asn Ala Phe Ile Pro Val Pro
705                 710                 715                 720

Ala Leu Thr Pro Ala Ser Leu Ile Ile Glu Asp Asn Asn Tyr Gly Asp
                725                 730                 735
```

-continued

```
Asn Asn Ile Ser Ile Leu Ala Pro Thr Asn Asn Asp Met Phe Met Leu
            740                 745                 750
Pro Gly Asn Val Tyr Pro Val Glu Ile Glu Thr Lys Val Ser Val Ser
            755                 760                 765
Tyr Ile Gly Arg Gly Phe Asp Pro Asn Gly Thr Pro Leu Ser Gly Ala
            770                 775                 780
His Val Leu Asn Glu Pro His Val Ile Leu Asp Glu Asp Gly Gly Phe
785                 790                 795                 800
Ser Phe Glu Tyr Thr Gly Asn Glu Lys Thr Leu Phe Leu Leu Lys Gly
                805                 810                 815
Arg Thr Ile Tyr Thr Cys Gln Leu Gly Lys Asn Lys Val His Lys Gly
                820                 825                 830
Ile Val Phe Val Gly Asp Val Ile Cys Asp Ile Asn Ser Thr Ser Ser
                835                 840                 845
Leu Pro Asp Glu Phe Val Lys Asn Pro Arg Val Gln Asp Leu Leu Ala
                850                 855                 860
Lys Asn Asp Lys Gly
865
```

(2) INFORMATION FOR SEQ ID NO:16:

(i) SEQUENCE CHARACTERISTICS:
   (A) LENGTH: 363 amino acids
   (B) TYPE: amino acid
   (C) STRANDEDNESS:
   (D) TOPOLOGY: unknown (ii) MOLECULE TYPE: protein (iii) HYPOTHETICAL: NO (xi) SEQUENCE DESCRIPTION: SEQ ID NO:16:

```
Met Lys Lys Ile Phe Ile Phe Leu Ser Ile Ile Phe Ser Ala Val Val
1               5                   10                  15
Ser Ala Gly Arg Tyr Pro Glu Thr Thr Val Gly Asn Leu Thr Lys Ser
                20                  25                  30
Phe Gln Ala Pro Arg Leu Asp Arg Ser Val Gln Ser Pro Ile Tyr Asn
                35                  40                  45
Ile Phe Thr Asn His Val Ala Gly Tyr Ser Leu Ser His Ser Leu Tyr
            50                  55                  60
Asp Arg Ile Val Phe Leu Cys Thr Ser Ser Asn Pro Val Asn Gly
65                  70                  75                  80
Ala Cys Pro Thr Ile Gly Thr Ser Gly Val Gln Tyr Gly Thr Thr Thr
                85                  90                  95
Ile Thr Leu Gln Phe Thr Glu Lys Arg Ser Leu Ile Lys Arg Asn Ile
                100                 105                 110
Asn Leu Ala Gly Asn Lys Lys Pro Ile Trp Glu Asn Gln Ser Cys Asp
                115                 120                 125
Phe Ser Asn Leu Met Val Leu Asn Ser Lys Ser Trp Ser Cys Gly Ala
                130                 135                 140
His Gly Asn Ala Asn Gly Thr Leu Leu Asn Leu Tyr Ile Pro Ala Gly
145                 150                 155                 160
Glu Ile Asn Lys Leu Pro Phe Gly Gly Ile Trp Glu Ala Thr Leu Ile
                165                 170                 175
Leu Arg Leu Ser Arg Tyr Gly Val Ser Ser Thr His Tyr Gly Asn
                180                 185                 190
Tyr Thr Val Asn Ile Thr Val Asp Leu Thr Asp Lys Gly Asn Ile Gln
```

-continued

```
                 195                 200                 205
    Val Trp Leu Pro Gly Phe His Ser Asn Pro Arg Val Asp Leu Asn Leu
        210                 215                 220

Arg Pro Ile Gly Asn Tyr Lys Tyr Ser Gly Ser Asn Ser Leu Asp Met
    225                 230                 235                 240

Cys Phe Tyr Asp Gly Tyr Ser Thr Asn Ser Asp Ser Met Val Ile Lys
                    245                 250                 255

Phe Gln Asp Asp Asn Pro Thr Asn Ser Ser Glu Tyr Asn Leu Tyr Lys
                260                 265                 270

Ile Gly Gly Thr Glu Lys Leu Pro Tyr Ala Val Ser Leu Leu Met Gly
                275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
    305                 310                 315                 320

Pro Glu Val Asn Val Pro Val Leu Cys Trp Pro Ala Arg Leu Leu Leu
                    325                 330                 335

Asn Ala Asp Val Asn Asn Pro Glu Ala Gly Gln Tyr Met Gly Asn Ile
                340                 345                 350

Lys Ile Thr Phe Thr Pro Ser Ser Gln Thr Leu
                355                 360
```

(2) INFORMATION FOR SEQ ID NO:17:

(i) SEQUENCE CHARACTERISTICS:
        (A) LENGTH: 360 amino acids
        (B) TYPE: amino acid
        (C) STRANDEDNESS:
        (D) TOPOLOGY: unknown (ii) MOLECULE TYPE: protein (iii) HYPOTHETICAL: NO (xi) SEQUENCE DESCRIPTION: SEQ ID NO:17:

```
    Met Asn Lys Ile Leu Phe Ile Phe Thr Leu Phe Phe Ser Ser Gly Phe
    1               5                   10                  15

Phe Thr Phe Ala Val Ser Ala Asp Lys Asn Pro Gly Ser Glu Asn Met
                    20                  25                  30

Thr Asn Thr Ile Gly Pro His Asp Arg Gly Gly Ser Ser Pro Ile Tyr
                35                  40                  45

Asn Ile Leu Asn Ser Tyr Leu Thr Ala Tyr Asn Gly Ser His His Leu
        50                  55                  60

Tyr Asp Arg Met Ser Phe Leu Cys Leu Ser Ser Gln Asn Thr Leu Asn
    65                  70                  75                  80

Gly Ala Cys Pro Ser Ser Asp Ala Pro Gly Thr Ala Thr Ile Asp Gly
                    85                  90                  95

Glu Thr Asn Ile Thr Leu Gln Phe Thr Glu Lys Arg Ser Leu Ile Lys
                100                 105                 110

Arg Glu Leu Gln Ile Lys Gly Tyr Lys Gln Phe Leu Phe Lys Asn Ala
            115                 120                 125

Asn Cys Pro Ser Lys Leu Ala Leu Asn Ser Ser His Phe Gln Cys Asn
        130                 135                 140

Arg Glu Gln Ala Ser Gly Ala Thr Leu Ser Leu Tyr Ile Pro Ala Gly
    145                 150                 155                 160

Glu Leu Asn Lys Leu Pro Phe Gly Gly Val Trp Asn Ala Val Leu Lys
                    165                 170                 175
```

-continued

```
Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
            275                 280                 285

Asn Leu Thr Pro Thr Asn Gly Gln Ala Leu Asn Ile Asn Thr Ala Ser
        290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Glu Tyr Ser Gly Ile Leu Asn Val Thr
            340                 345                 350

Phe Thr Pro Ser Ser Ser Ser Leu
        355             360
```